United States Patent [19]
Zupi

[11] Patent Number: 6,080,727
[45] Date of Patent: Jun. 27, 2000

[54] OLIGONUCLEOTIDE TREATMENTS AND COMPOSITIONS FOR HUMAN MELANOMA

[75] Inventor: Gabriella Zupi, Rome, Italy

[73] Assignee: Istituto Regina Elena, Rome, Italy

[21] Appl. No.: 08/827,036

[22] Filed: Mar. 25, 1997

Related U.S. Application Data

[60] Provisional application No. 60/014,089, Mar. 26, 1996.

[51] Int. Cl.$^7$ .............................. A61K 31/70; C07H 21/00
[52] U.S. Cl. ............................. 514/44; 435/375; 536/24.5
[58] Field of Search ................................ 435/6, 325, 366, 435/375, 377; 514/44; 424/649; 536/24.31, 24.5; 935/34

[56] References Cited

U.S. PATENT DOCUMENTS

| | | | |
|---|---|---|---|
| 4,415,732 | 11/1983 | Caruthers et al. | 536/26.5 |
| 4,458,066 | 7/1984 | Caruthers et al. | 536/25.34 |
| 4,469,863 | 9/1984 | Ts'o et al. | 536/24.5 |
| 4,725,677 | 2/1988 | Koster et al. | 536/25.34 |
| 4,757,055 | 7/1988 | Miller et al. | 514/44 |
| 4,806,463 | 2/1989 | Goodchild et al. | 435/5 |
| 4,973,679 | 11/1990 | Caruthers et al. | 536/26.71 |
| 4,980,460 | 12/1990 | Moloko et al. | 536/26.71 |
| 5,130,302 | 7/1992 | Speilvogel et al. | 514/45 |
| 5,151,510 | 9/1992 | Stec et al. | 536/25.3 |
| 5,166,387 | 11/1992 | Hirschbein | 558/129 |
| 5,183,885 | 2/1993 | Bergot | 536/25.41 |
| 5,585,479 | 12/1996 | Hoke et al. | 536/24.5 |

FOREIGN PATENT DOCUMENTS

| | | |
|---|---|---|
| 89/11486 | 11/1983 | WIPO. |
| 90/15065 | 12/1990 | WIPO. |
| 91/04753 | 4/1991 | WIPO. |
| 92/05186 | 4/1992 | WIPO. |
| 92/20703 | 11/1992 | WIPO. |
| 93/01286 | 1/1993 | WIPO. |
| 95/25814 | 9/1995 | WIPO. |
| 96/39531 | 12/1996 | WIPO. |

OTHER PUBLICATIONS

Ahern et al. Overexpression of c–erbB–2 and c–myc but not c–ras, in canine melanoma cell lines, is associated with metastatic potential in nude mice. Anticancer Res. 13: 1365–1372, 1993.

Gewirtz et al. Facilitating oligonucleotide delivery: Helping antisense deliver on its promise. Proc. Natl. Acad. Sci. USA 93, 3161–3163, Apr. 1996.

Osanto et al. Downmodulation of c–myc expression by interferon and tumour necrosis factor precedes growth arrest in human melanoma cells. Eur. J. Cancer, 28A: 1622–1627, 1992.

Zon et al. "Phosphorothioate oligonucleotides" in Oligonucleotides and Analogues, Eckstein, ed. IRL Press, New York, pp. 87–108, 1991.

Leonetti, et al., "Antitumor effect of c–myc antisense phosphorothioate oligodeoxynucleotides on human melanoma cells in vitro and in mice", *J. Nat. Cancer Institute*, 88(7):421–429 (Apr. 3, 1996).

Agrawal et al., Proc. Natl. Acad. Sci. USA, vol. 88:7595–7599 (1991).
Arad et al., Biochem. Biophy. Acta., vol. 859: 88–94 (1986).
Battey et al., Cell, vol. 34:779–787 (1993).
Beal and Dervan, J. Am. Chem. Soc., vol. 114:4976–4982 (1982).
Beal and Dervan, Nucleic Acids Research, vol. 20:2773–2776 (1992).
Beacage and Iyer, Tetrahedron, vol. 48:2223–2311 (1992).
Branda et al., Biochem. Phramacol., vol. 45:2037–2043 (1993).
Biro S., et al., "Inhibitory effects of antisense oligodeoxynucleotides targeting c–myc mRNA on smooth muscle cell proliferation and migration," Proc. Natl. Sci., vol. 90:654–658 (1993).
Blume et al., Nucleic Acids Research, vol. 20:1777–1784 (1992).
Chenevix–Trench et al., Oncogene, vol. 5:1887–1193 (1990).
Cheng et al., J. Am. Chem. Soc., vol. 114:4465–4474 (1992).
Chomczsky et al., Anal. Biochem., vol. 162:156–159 (1987).
Citro et al., Proc. Natl. Acad. Sci. USA, vol. 89:7031–7035 (1992).
Crooke, Ann. Rev. Pharmacol. Toxicol., vol. 32:329–376 (1992).
Dagle et al., Antisense Rev. Dev., vol. 1:11–20 (1991).
Distefano et al., Proc. Natl. Acad. Sci. USA., vol. 90:1179–1183 (1993).
Dugaiaczyk et al., Biochemistry, vol. 22:1605–1613 (1983).
Elsas, A.V., et al., "ras Oncogene Activation Does Not Induce Sensitivity to Natural Killer Cell–Mediated Lysis in Human Melanoma,"The Journal of Investigative Dermatology, vol. 103, No. 5:117S–121S (1994).
Evan et al., Mol. Cell Biol., vol. 5:3610–3616 (1985).
Finberg et al., Anal. Biochem., vol. 132:6.
Froehler et al., Tetrahedron Lett., vol. 33:5307–5310 (1992).
Gazin et al., E.M.B.O. Journal., vol. 32:383–387 (1984).
Geran et al., Cancer Chemother. Rep., vol. 3:1–88 (1972).
Giovannangeli et al., Proc. Natl. Acad. Sci. USA, vol. 89:8631–8635 (1992).

(List continued on next page.)

*Primary Examiner*—John S. Brusca
*Assistant Examiner*—Thomas G. Larson
*Attorney, Agent, or Firm*—Townsend and Townsend and Crew LLP

[57] ABSTRACT

The invention generally provides for compositions and methods of inhibiting the proliferation of human melanoma cancer cells. By administering a therapeutically effective amount of a c-myc oligonucleotide to a human melanoma cancer cell, melanoma cancer cell proliferation can be arrested or inhibited, metastases reduced from a tumor, and apoptosis induced in melanoma cancer cells. Oligonucleotides that are complementary to c-myc polynucleotides are referred to herein as "c-myc oligonucleotides." A particularly efficacious embodiment of the invention relates to compositions and methods concerning the co-administration of c-myc oligonucleotides and cisplatin.

48 Claims, 11 Drawing Sheets

OTHER PUBLICATIONS

Greco et al., Anticancer Res., vol. 7:839–844 (1987).

Greco et al., Tumori, vol. 65:169–180 (1979).

Hijiya et al., Proc. Natl. Acad. Sci. USA, vol. 91:4499–4503 (1994).

Lurquin "Incorporation of Drugs, Proteins and Genetic Material," Liposome Technology, vol. II, Gregoriadis, ed. (CRC press), pp. 187–221 (1984).

Krieg et al., Nature, vol. 374:546–549 (1995).

Lemaiture et al., Proc. Natl. Acal. Sci. USA, vol. 84:648–652 (1987).

Lesinkowski, Bioinorganic Chemistry, vol. 21:127–155 (1993).

Letsinger et al., Proc. Natl. Acad. Sci., vol. 86:6553–6556 (1989).

Lombardi et al., Cell, vol. 49:161–170 (1987).

Marcu et al., Ann. Rev. Biochem., vol. 61:809–860 (1992).

Marshall et al., Science, vol. 259:1564–1570 (1993).

McShan et al., J. Biol. Chem., vol. 267:5712–5721 (1992).

Mergny et al., Biochemistry, vol. 30:9791–9798 (1991).

Milligan et al., J. Med. Chem., vol. 36:1923–1937 (1993).

Mitzutani, Y., et al., "Enhanced Susceptibility to c–myc Antisense Oligonucleotide–Treated Human Renal Cell Carcinoma Cells to Lysis by Peripheral Blood Lymphocytes," J. of Immunotherapy, vol. 17:78–87 (1995).

Mitzutani, Y., et al., "Enhancement of Sensitivity of Urinary Bladder Tumor Cells to Cisplatin by Cisplatin by c–myc Antisense Oligonucleotide," Cancer, vol. 74, No. 9:2546–2554 (1994).

Mojcik et al., Clin. Immunol. Immunopathol., vol. 67:130–136 (1993).

Moser and Dervan, Science, vol. 238:645–650 (1987).

Mottolese et al., Melanoma Res., vol. 4:53–58 (1994).

Neiborrow–Skorska, M., et al, "Oncogene–targeted antisense olgodeoxynucleotides combined with chemotherapy or immunotherapy: A new approach for tumor treatment," Folia Histochemica, vol. 32, No. 1:35–40 (1994).

Neilsen et al., Anti–cancer Drug Design, vol. 8:53–63, 1993 (International application PCT/EP92/01220).

Normanno, N., Bianco, C., et al., "Growth Inhibition of Human Colon Carcinoma Cells By Combinations of Anti-–Epidermal Growth Factor–related Growth Factor Antisense Olgonucleotides," Clinical Cancer Research, vol. 2:601–609 (1996).

Peltenburg, L.T.C., Schrier, P.I., "Transcriptional suppression of HLA–B expression by c–Myc is mediated through the core promoter elements," Immunogenetics, vol. 40:54–61 (1994).

Roberts et al., Proc. Natl. Acad. Sci. USA., vol. 88:9397–9401 (1991).

Roberts et al., Science, vol. 258:1463–1466 (1992).

Shea et al., Nucleic Acids Research, vol. 18:3777–3783 (1990).

Stein, C.A., "Antitumor Effects of Antisense Phosphorothiolate c–myc Oligodeoxynucleotides: a Question of Mechanism," J. Natl. Cancer Inst., vol. 88:391–393 (1996).

Stein et al., Nucleic Acid Res., vol. 16:3209–3221 (1988).

Szostak et al., Meth. Enzymol., vol. 68:419–429 (1979).

Ulmann et al., Chemical Reviews, vol. 90:543–584 (1990).

Versteeg, P., "C–myc down–regulates class 1 HLA expression in human melanomas," The EMBO Journal, vol. 7, No. 4:1023–1029 (1988).

Wagner et al., Proc. Natl. Acad. Sci. USA, vol. 87:3410–3414 (1990).

Walker, T.L., "Tumor cells surviving in vivo cisplatin chemotherapy dislpay elevated cmyc expression," 610–614 (1995).

Watt et al., Nature, vol. 303:725–728 (1983).

Whartenby, K.A., et al., "Biology of Disease," Laboratory Investigation, vol. 72, No. 2:131–145 (1995).

Wickstrom et al., J. Biochem. Biophys. Methods, vol. 13:97–102 (1987).

Yaswen et al., Antisense Res. Dev., vol. 3:67–77 (1993).

Yoon et al., Proc. Natl. Acad. Sci., vol. 75:280–284 (1974).

Zamecnik and Stephenson, Proc. Natl. Acad. Sci., vol. 75:280–284 (1974).

Zon and Geiser, Anti–Cancer Drug Design, vol. 6:539–568 (1991).

Zupi et al., Proc. Am. Assoc. Cancer Res., vol. 26:22 (1985).

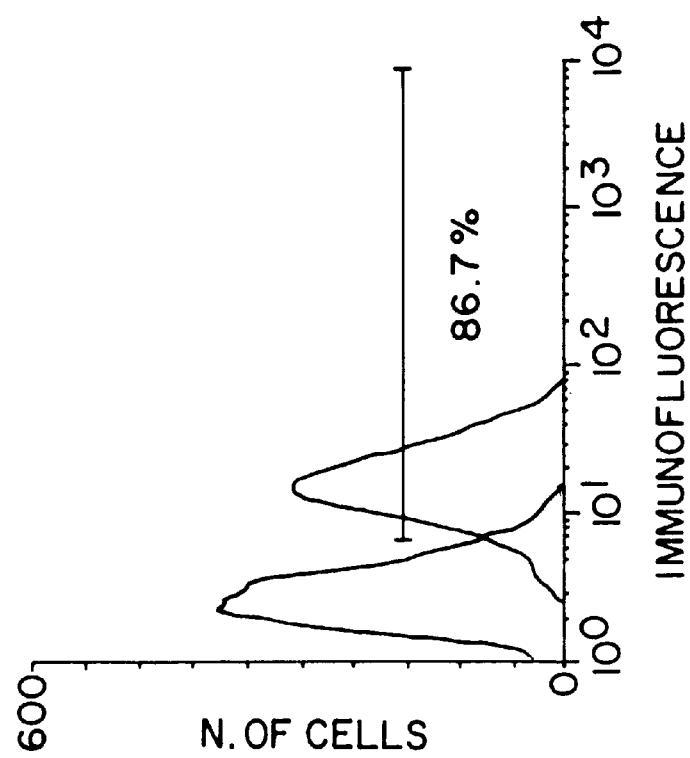
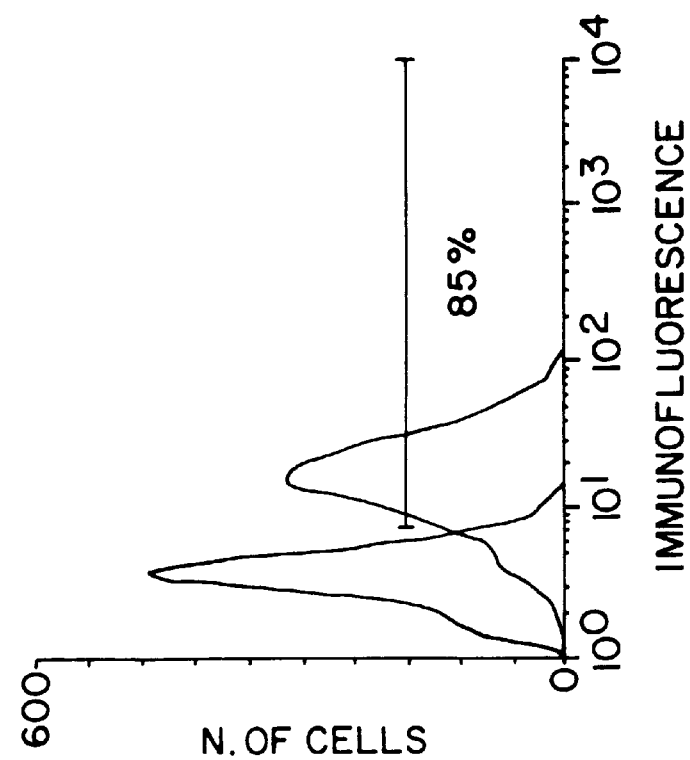

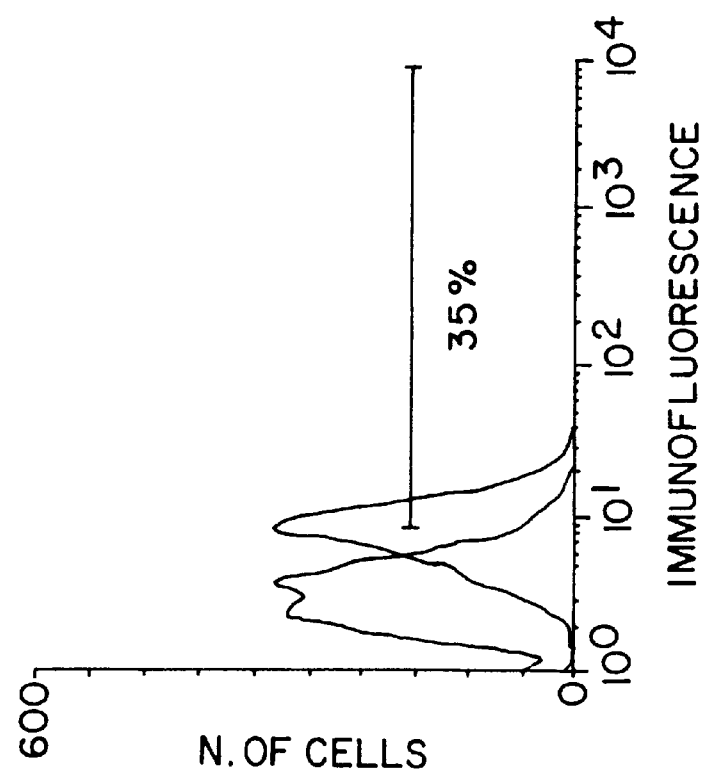
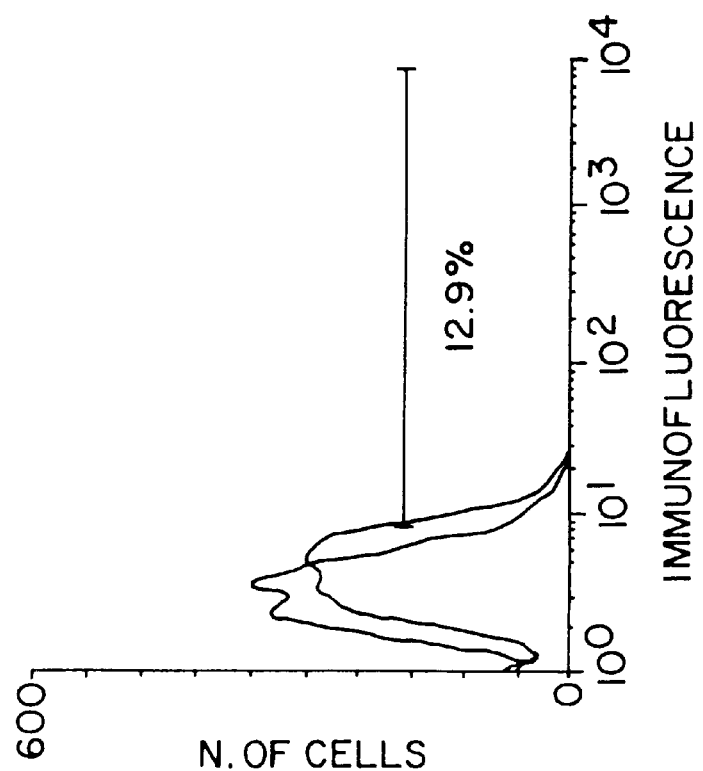

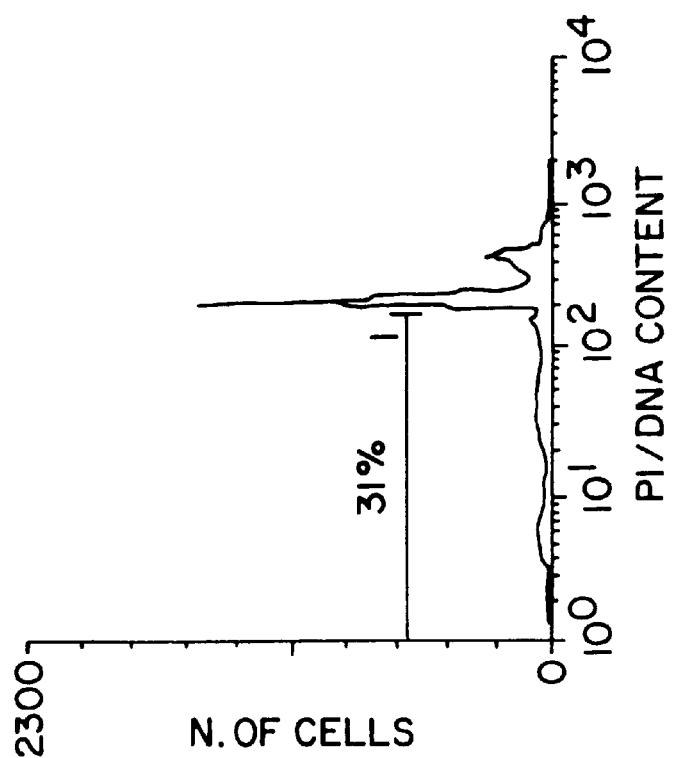
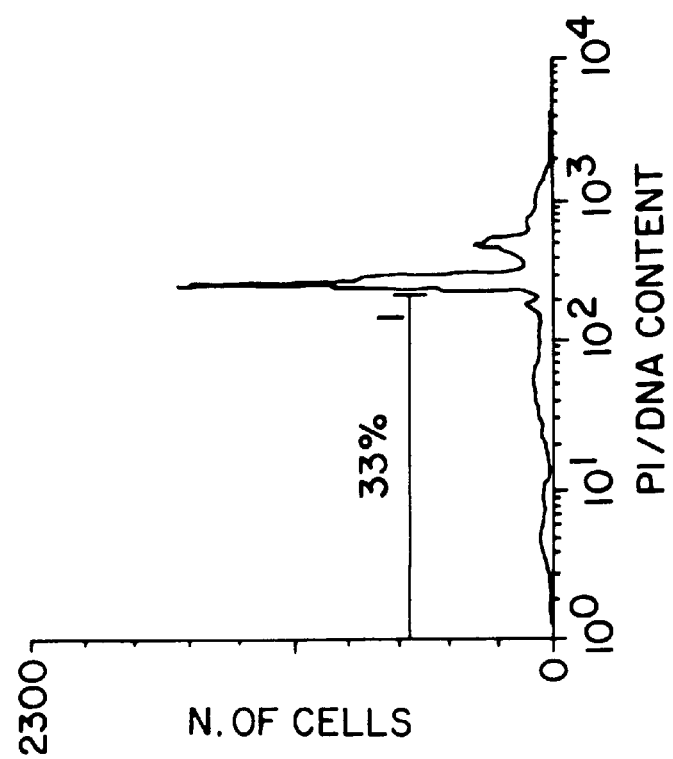

SEQUENCE LISTING (1) GENERAL INFORMATION:

(iii) NUMBER OF SEQUENCES: 18

(2) INFORMATION FOR SEQ ID NO: 1:

(i) SEQUENCE CHARACTERISTICS:
        (A) LENGTH: 15 nucleotides
        (B) TYPE: nucleic acid
        (C) STRANDEDNESS: single
        (D) TOPOLOGY: linear (xi) SEQUENCE DESCRIPTION: SEQ ID NO: 1:

AACGTTGAGG GGCAT        15

(2) INFORMATION FOR SEQ ID NO: 2:

(i) SEQUENCE CHARACTERISTICS:
        (A) LENGTH: 15 nucleotides
        (B) TYPE: nucleic acid
        (C) STRANDEDNESS: single
        (D) TOPOLOGY: linear (xi) SEQUENCE DESCRIPTION: SEQ ID NO: 2:

ATGCCCCTCA ACGTT        15

(2) INFORMATION FOR SEQ ID NO: 3:

(i) SEQUENCE CHARACTERISTICS:
        (A) LENGTH: 15 nucleotides
        (B) TYPE: nucleic acid
        (C) STRANDEDNESS: single
        (D) TOPOLOGY: linear (xi) SEQUENCE DESCRIPTION: SEQ ID NO: 3:

AACGTGGATT GGCAG        15

(2) INFORMATION FOR SEQ ID NO: 4:

(i) SEQUENCE CHARACTERISTICS:
        (A) LENGTH: 15 nucleotides
        (B) TYPE: nucleic acid
        (C) STRANDEDNESS: single
        (D) TOPOLOGY: linear (xi) SEQUENCE DESCRIPTION: SEQ ID NO: 4:

AAGCATACGG GGTGT        15

(2) INFORMATION FOR SEQ ID NO: 5:

(i) SEQUENCE CHARACTERISTICS:
        (A) LENGTH: 15 nucleotides
        (B) TYPE: nucleic acid
        (C) STRANDEDNESS: single
        (D) TOPOLOGY: linear (xi) SEQUENCE DESCRIPTION: SEQ ID NO: 5:

AACGTTGAGG GGCAT        15

(2) INFORMATION FOR SEQ ID NO: 6:

(i) SEQUENCE CHARACTERISTICS:
        (A) LENGTH: 20 nucleotides
        (B) TYPE: nucleic acid
        (C) STRANDEDNESS: single
        (D) TOPOLOGY: linear (xi) SEQUENCE DESCRIPTION: SEQ ID NO: 6:

GGCCTTTTCA TTGTTTTCCA        20

```
(2) INFORMATION FOR SEQ ID NO: 7:

(i) SEQUENCE CHARACTERISTICS:
        (A) LENGTH:  20 nucleotides
        (B) TYPE:  nucleic acid
        (C) STRANDEDNESS:  single
        (D) TOPOLOGY:  linear (xi) SEQUENCE DESCRIPTION: SEQ ID NO: 7:

AAAGTGCCCG CCCGCTGCTA                                                    20

(2) INFORMATION FOR SEQ ID NO: 8:

(i) SEQUENCE CHARACTERISTICS:
        (A) LENGTH:  20 nucleotides
        (B) TYPE:  nucleic acid
        (C) STRANDEDNESS:  single
        (D) TOPOLOGY:  linear (xi) SEQUENCE DESCRIPTION: SEQ ID NO: 8:

CCAGTGCAAA GTGCCCGCCC                                                    20

(2) INFORMATION FOR SEQ ID NO: 9:

(i) SEQUENCE CHARACTERISTICS:
        (A) LENGTH:  20 nucleotides
        (B) TYPE:  nucleic acid
        (C) STRANDEDNESS:  single
        (D) TOPOLOGY:  linear (xi) SEQUENCE DESCRIPTION: SEQ ID NO: 9:

GGGAGAGTCG CGTCCTTGCT                                                    20

(2) INFORMATION FOR SEQ ID NO: 10:

(i) SEQUENCE CHARACTERISTICS:
        (A) LENGTH:  20 nucleotides
        (B) TYPE:  nucleic acid
        (C) STRANDEDNESS:  single
        (D) TOPOLOGY:  linear (xi) SEQUENCE DESCRIPTION: SEQ ID NO: 10:

TCATGGAGCA CCAGGGGCTC                                                    20

(2) INFORMATION FOR SEQ ID NO: 11:

(i) SEQUENCE CHARACTERISTICS:
        (A) LENGTH:  20 nucleotides
        (B) TYPE:  nucleic acid
        (C) STRANDEDNESS:  single
        (D) TOPOLOGY:  linear (xi) SEQUENCE DESCRIPTION: SEQ ID NO: 11:

CGTTCTTTTT TCCCGCCAAG                                                    20

(2) INFORMATION FOR SEQ ID NO: 12:

(i) SEQUENCE CHARACTERISTICS:
        (A) LENGTH:  17 nucleotides
        (B) TYPE:  nucleic acid
        (C) STRANDEDNESS:  single
        (D) TOPOLOGY:  linear (xi) SEQUENCE DESCRIPTION: SEQ ID NO: 12:

CATTGTTTTC CAACTCC                                                       17

(2) INFORMATION FOR SEQ ID NO: 13:
```

```
    (i) SEQUENCE CHARACTERISTICS:
         (A) LENGTH:  20 nucleotides
         (B) TYPE:  nucleic acid
         (C) STRANDEDNESS:  single
         (D) TOPOLOGY:  linear (xi) SEQUENCE DESCRIPTION: SEQ ID NO: 13:

TGATGGAGCA CCAGGGGCTC                                                      20

(2) INFORMATION FOR SEQ ID NO: 14:

(i) SEQUENCE CHARACTERISTICS:
         (A) LENGTH:  15 nucleotides
         (B) TYPE:  nucleic acid
         (C) STRANDEDNESS:  single
         (D) TOPOLOGY:  linear (xi) SEQUENCE DESCRIPTION: SEQ ID NO: 14:

GAGCACCAGG GGCTC                                                           15

(2) INFORMATION FOR SEQ ID NO: 15:

(i) SEQUENCE CHARACTERISTICS:
         (A) LENGTH:  15 nucleotides
         (B) TYPE:  nucleic acid
         (C) STRANDEDNESS:  single
         (D) TOPOLOGY:  linear (xi) SEQUENCE DESCRIPTION: SEQ ID NO: 15:

GGAGCACCAG GGGCT                                                           15

(2) INFORMATION FOR SEQ ID NO: 16:

(i) SEQUENCE CHARACTERISTICS:
         (A) LENGTH:  15 nucleotides
         (B) TYPE:  nucleic acid
         (C) STRANDEDNESS:  single
         (D) TOPOLOGY:  linear (xi) SEQUENCE DESCRIPTION: SEQ ID NO: 16:

TGGAGCACCA GGGGC                                                           15

(2) INFORMATION FOR SEQ ID NO: 17:

(i) SEQUENCE CHARACTERISTICS:
         (A) LENGTH:  15 nucleotides
         (B) TYPE:  nucleic acid
         (C) STRANDEDNESS:  single
         (D) TOPOLOGY:  linear (xi) SEQUENCE DESCRIPTION: SEQ ID NO: 17:

ATGGAGCACC AGGGG                                                           15

(2) INFORMATION FOR SEQ ID NO: 18:

(i) SEQUENCE CHARACTERISTICS:
         (A) LENGTH:  53 nucleotides
         (B) TYPE:  nucleic acid
         (C) STRANDEDNESS:  single
         (D) TOPOLOGY:  linear (xi) SEQUENCE DESCRIPTION: SEQ ID NO: 18:

CCCGCTCCAG CAGCCTCCCG CGACGATGCCC CTCAACGTT                                40

AGCTTCACCA ACA                                                             53
```

OLIGONUCLEOTIDE TREATMENTS AND COMPOSITIONS FOR HUMAN MELANOMA

This application claims the benefit of U.S. Provisional Application Ser. No. 60/014,089, filed Mar. 26, 1996.

TECHNICAL FIELD

The present invention relates to compositions and methods for treating melanoma based on oligonucleotides complementary to c-myc polynucleotides and co-administration of such oligonucleotides with cisplatin.

BACKGROUND

Melanoma tumors are a growing health concern to millions of people worldwide. Because the growth of tumors is influenced by many factors, including the activation of multiple oncogenes, such as proto-oncogenes, it has been difficult to ascertain the cellular mechanisms underlying cancer cell biology. Consequently, available therapies are limited in their ability to arrest tumor growth from human melanoma cancer cells.

In the case of melanoma, the c-myc proto-oncogene is expressed in human melanoma cancer cells growing as tumors. The contribution of this proto-oncogene to the development of melanoma in humans has remained unelucidated until the present invention. For instance, it has been not understood, until the present invention, whether c-myc expression is necessary for melanoma cancer cell proliferation, whether c-myc expression plays a minor role in melanoma cancer cell proliferation or whether c-myc expression is a result of melanoma cancer cell proliferation rather than the cause the of melanoma cell proliferation. The role of c-myc expression in melanoma metastasis and apoptosis has been also not understood. Nor has the role of c-myc expression been established for the chemoresistance of melanoma to cisplatin.

Consequently, it would be desirable to provide therapeutic compositions and methods to thwart the progression of melanoma cancer in humans, which is the result of multiple cellular processes in human melanoma cancer cells.

SUMMARY OF THE INVENTION

The invention generally provides for compositions and methods of inhibiting the proliferation of human melanoma cancer cells. By administering a therapeutically effective amount of a c-myc oligonucleotide to a human melanoma cancer cell, melanoma cancer cell proliferation can be arrested or inhibited, metastases reduced from a tumor, and apoptosis induced in melanoma cancer cells. Oligonucleotides that are complementary to c-myc polynucleotides are referred to herein as "c-myc oligonucleotides." A particularly efficacious embodiment of the invention relates to compositions and methods concerning the co-administration of c-myc oligonucleotides and cisplatin.

| slope values | | | | |
|---|---|---|---|---|
| Panel A | | | | |
| control (c) | | | 72 | |
| c-myc (S)ODNs | (a1) 0.25 mg | | 33 | vs c p < .00005; vs s1 p < .00005 |
| | (a2) 0.5 mg | | 31 | vs c p < .00005; vs a1 p = 0.31; vs s2 p < .00005 |
| | (a3) 1 mg | | 8 | vs c p < .00005; vs a1 p < .00005; vs a2 p = .00044; vs s3 p < .0000_ |
| scrambled | (s1) 0.25 mg | | 69 | vs c p = 0.91 |
| | (s2) 0.5mg | | 72 | vs c p = 0.99 |
| | (s3) 1 mg | | 66 | vs c p = 0.86 |

-continued

| | | slope values | |
|---|---|---|---|
| Panel B | | | |
| control (c) | | 50 | |
| c-myc (S)ODNs | (a1) 0.25 mg | 19 | vs c p < .00005; vs s1 p < .00005 |
| | (a2) 0.5 mg | 15 | vs c p < .00005; vs s2 p < .00005; vs a1 p = 0.16 |
| scrambled | (s1) 0.25 mg | 50 | vs c p = 0.99 |
| | (s2) 0.5 mg | 43 | vs c p = 0.26 |
| Panel C | | | |
| control (c) | | 113 | |
| c-myc (S)ODNs (a) | | 12 | vs c p < .00005; vs s p < .00005 |
| scrambled (s) | | 105 | vs c p = 0.15 |

Figure 4H:
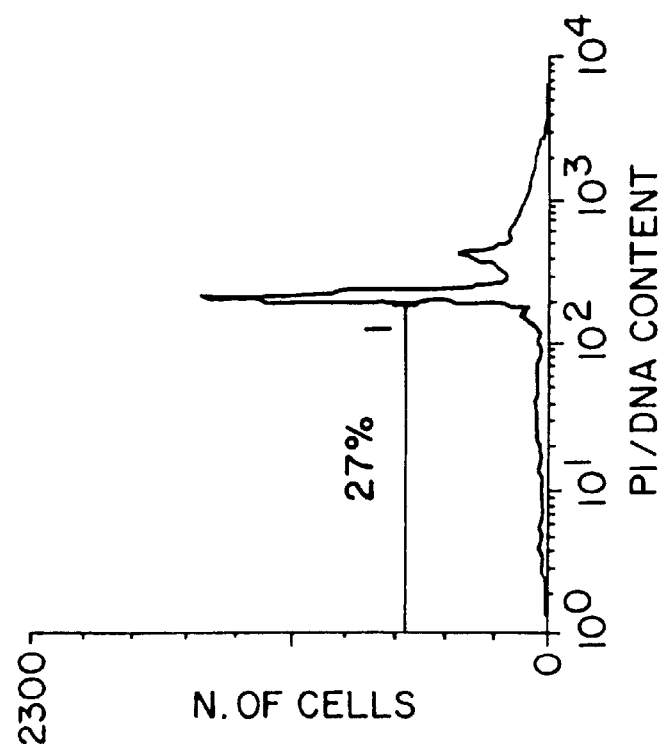

FIGS. 4A–4H show flow cytometric analysis of c-myc expression in NG tumor tissue obtained from mice that are treated with (S)ODNs targeted to c-myc according to schedule c (see Table 3). Panels: FIGS. 4A and 4E untreated (A), FIGS. 4B and 4F scrambled-(B) FIGS. 4C and 4G antisense-(C), and FIGS. 4d and 4H 2.5 mg antisense (on day 23)-treated mice (D); percentages indicate proportion of cells expressing c-myc protein. Inserts (FIGS. 4E,4F,4G,4H) show DNA-content (propidium iodide staining) analyses; percentages indicate proportion of cells with a subdiploid DNA content.

Figure 5:
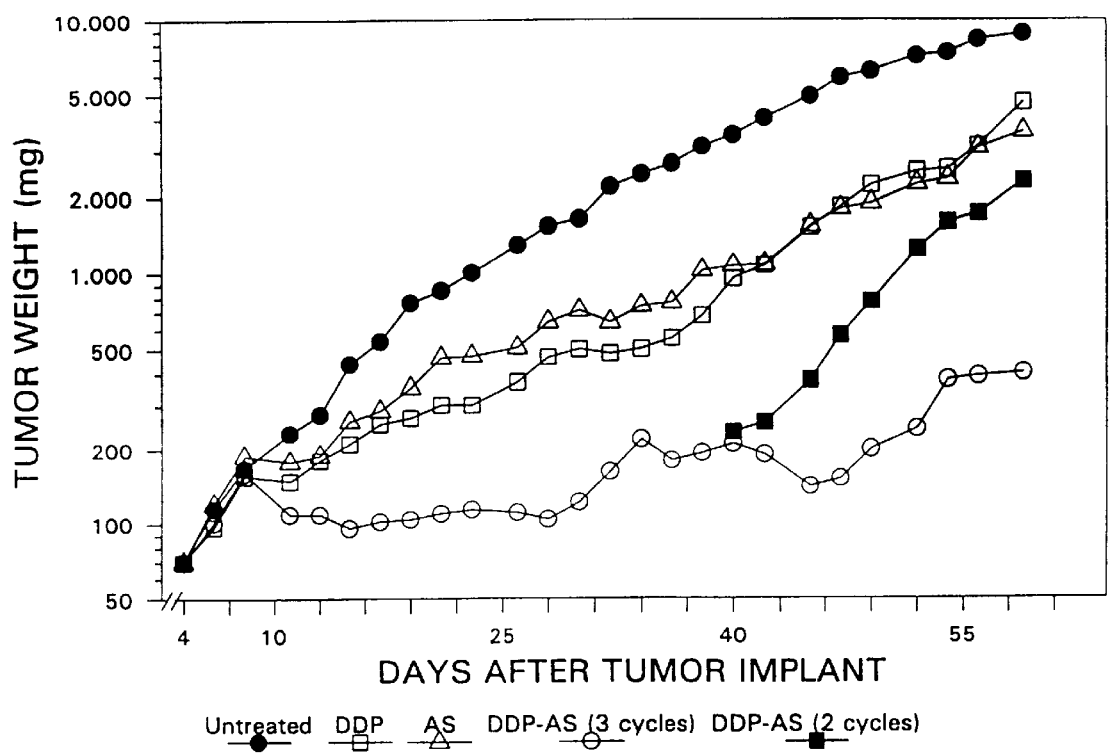

FIG. 5 shows the growth of tumors from cells that are implanted into mice treated with c-myc oligonucleotide in combination with cisplatin. Panels: (●) Untreated; (□) cisplatin intraperitoneal 3.3 mg/Kg days 4–6; (△) c-myc (S)ODNs intravenous 1 mg/mouse at days 7, 9, 11, 13 and 0.5 mg/mouse at days 8, 10, 12, 14; (■) cisplatin days 4–6 followed by c-myc (S)ODNs days 7–14. A second cycle of treatment was administered after a 7-day interval. Mice treated with the combination schedule were randomized in two groups and one group (○) received a third cycle of combination treatment after a 7-day interval. This third cycle started on day 40.

DESCRIPTION OF SPECIFIC EMBODIMENTS
Definitions

The term "complementary" or "reverse complement" as used herein reflect the ability of an oligonucleotide to form a duplex or triplex with a target sequence. Preferably, the oligonucleotide can form a duplex with a mRNA encoding a protein involved in the pathology of melanoma, such as, for example, c-myc. An oligonucleotide complementary to c-myc mRNA is capable of binding to c-myc mRNA by way of a regular pattern of monomer-to-monomer interactions, such as Watson-Crick type of base pairing, Hoogsteen or reverse Hoogsteen types of base pairing, or the like. For example, the sequence of SEQ ID NO.: 1 is complementary to and is the reverse of complement of the sequence of SEQ ID NO.: 2. Alternatively, triplex formation can occur between an oligonucleotide that is complementary to c-myc genomic DNA.

The term "nucleoside" as used herein includes the natural nucleosides, including 2'-deoxy and 2'-hydroxyl forms, e.g. as described in Kornberg and Baker, DNA Replication, 2nd Ed. (Freeman, San Francisco, 1992). "Analogs" in reference to nucleosides includes synthetic nucleosides having modified base moieties and/or modified sugar moieties, e.g. described generally by Scheit, Nucleotide Analogs (John Wiley, New York, 1980). Such analogs include synthetic nucleosides designed to enhance binding properties, e.g. duplex or triplex stability, specificity, or the like.

The term "oligonucleotide" as used herein includes linear oligomers of natural or modified monomers or linkages, including deoxyribonucleosides, ribonucleosides, α-anomeric forms thereof, polyamide nucleic acids, and the like, capable of specifically binding to a target polynucleotide by way of a regular pattern of monomer-to-monomer interactions (e.g. nucleoside-to-nucleoside), such as Watson-Crick type of base pairing, Hoogsteen or reverse Hoogsteen types of base pairing, or the like. Usually monomers are linked by phosphodiester bonds or analogs thereof to form oligonucleotides ranging in size from a few monomeric units, e.g. 3–4, to several hundreds of monomeric units. Whenever an oligonucleotide is represented by a sequence of letters, such as "ATGCCTG," it will be Understood that the nucleotides are in 5'->3' order from left to right and that "A" denotes deoxyadenosine, "C" denotes deoxycytidine, "G" denotes deoxyguanosine, and "T" denotes thymidine, unless otherwise noted. Analogs of phosphodiester linkages include phosphorothioate, phosphorodithioate, phosphoroselenoate, phosphorodiselenoate, phosphoroanilothioate, phosphoranilidate, phosphoramidate, N3'→P5' phosphoramidate and the like, as more fully described herein.

The term "proliferation" when used in reference to cells refers to population growth of cells, such as in a culture or in formation or progression of a tumor. For example, cancer cells comprising a tumor can form additional tumor tissue by proliferation, as well as an increase in the mass of each individual tumor cell. Tumor formation by human melanoma cancer cells can occur in both non-syngenic mammals and syngenic mammals.

"Stability" in reference to duplex or triplex formation roughly means how tightly a complementary oligonucleotide binds to its intended target sequence; more precisely, it means the free energy of formation of the duplex or triplex under physiological conditions. Melting temperature under a standard set of conditions, e.g. as described below, is a convenient measure of duplex and/or triplex stability. Preferably, complementary oligonucleotides of the invention are selected that have melting temperatures of at least 50° C. under the standard conditions set forth herein; thus, under physiological conditions and the preferred concentrations, duplex or triplex formation will be substantially favored over the state in which the complementary oligonucleotide and its target are dissociated. It is understood that a stable duplex or triplex may in some embodiments include mismatches between base pairs and/or among base triplets in the case of triplexes (e.g. no more than one mismatch per 12 bases). Preferably, complementary oligonucleotides of the invention form perfectly matched duplexes and/or triplexes with their target polynucleotides, e.g. mRNA and genomic DNA.

Introduction

The invention generally provides for compositions and methods of inhibiting the proliferation of human melanoma cancer cells. By administering a therapeutically effective amount of a c-myc oligonucleotide to a human melanoma cancer cell, melanoma cancer cell proliferation can be arrested or inhibited, metastases reduced from a tumor, and apoptosis induced in melanoma cancer cells. Oligonucleotides that are complementary to c-myc polynucleotides are referred to herein as "c-myc oligonucleotides." A particularly efficacious embodiment of the invention relates to compositions and methods concerning the co-administration of c-myc oligonucleotides and cisplatin.

Prior to the invention, such compositions and methods were not available because the role of c-myc expression in human melanoma cancer cell proliferation had not been established. Described herein for the first time are experiments that demonstrate the necessity of c-myc expression for melanoma tumor growth and metastasis. Experiments described herein demonstrate that melanoma tumor growth and metastasis can be inhibited by the administration of c-myc oligonucleotides and that c-myc oligonucleotides induce apoptosis of melanoma cancer cells. Experiments described herein also demonstrate that chemoresistance of melanoma to cisplatin is reduced by the co-administration of c-myc oligonucleotides. The experiments described herein are not limited to the above discoveries. Such experiments and embodiments of the invention are discussed in more detail herein.

c-myc Oligonucleotides and Target Polynucleotides

The invention can be practiced utilizing oligonucleotides complementary to c-myc target polynucleotides. Such polynucleotides may be single stranded or double stranded DNA or RNA; however, double stranded DNA or single-stranded RNA targets are preferred. In a preferred embodiment, the invention uses an oligonucleotide having a sequence complementary to a region of c-myc mRNA. Nucleotides sequences can be selected for targeting as known in the art and described herein. The genomic nucleotide sequence and the mRNA transcripts of c-myc polynucleotides are known in the art and are described in Marcu et al, *Ann. Rev. Biochem.*, 61:809–860 (1992); Watt et al, *Nature*, 303:725–728 (1983); Battey et al, *Cell*, 34:779–787 (1983); and Biro et al, *Proc. Natl. Acad. Sci.*, 90: (1993).

There is substantial guidance in the literature for selecting particular sequences for complementary oligonucleotides given a knowledge of the sequence of the target polynucleotide, e.g. Ulmann et al, *Chemical Reviews*, 90:543–584 (1990); Crooke, *Ann. Rev. Pharmacol. Toxicol.* 32:329–376 (1992); and Zamecnik and Stephenson, *Proc. Natl. Acad. Sci*, 75:280–284 (1974). Preferably, the sequences of c-myc complementary compounds are selected so that the G-C content is at least 60%. Preferably sequences of the oligonucleotides are selected from 12 to 15 contiguous bases of SEQ. ID No. 1, 5, 9 or 10. Preferred mRNA targets include the 5' cap site, mRNA primer binding site, the initiation codon site, the mRNA donor splice site, the mRNA acceptor splice site, and the like, e.g. Goodchild et al, U.S. Pat. No. 4,806,463. It is understood that the target to which the c-myc oligonucleotides of the invention are directed can include allelic forms of the proto-oncogene.

When selecting complementary oligonucleotides to target the ATG initiation site of human c-myc in the second exon, complementary oligonucleotides with consecutive sequences can be administered using oligonucleotides 12, 13, 14, 15, 16, 17, 18, 19, 20, 21, 22, 23, 24, 25, 26, 27, 28, 29, 30, 31, 32, 33, 34, or 35 bases in length and selected from a twenty five base region on either side of the ATG site (human sequence from Gazin et al, *E.M.B.O. Journal* 32:383–387 (1984) the sequence of which in herein incorporated by reference):

5' cccgc tccagcagcc tcccgcgacg ATG cccctcaacg ttagct- tcac caaca 3' SEQ. ID NO.: 18. These oligonucleotide lengths can also be used for oligonucleotides that include other nucleotide sequences complementary c-myc polynucleotides. Such complementary nucleotide sequences are described herein, such as in the Sequence Listing. For instance, regions varying from 12 to 35 bases in length and partially or fully inclusive of SEQ ID No: 9 or 10 may be selected as an oligonucleotide. Preferably, complementary oligonucleotides will include the ATG site. The oligonucleotide preferably includes a nucleic acid sequence complementary to the translation initiation region of c-myc. The oligonucleotide of the invention can be an oligodeoxyribonucleotide (ODN), as well as an oligoribonucleotide, which is less preferred.

Oligonucleotides of the invention may comprise any polymeric compound capable of specifically binding to a target polynucleotide by way of a regular pattern of monomer-to-nucleoside interactions, such as Watson-Crick type of base pairing, Hoogsteen or reverse Hoogsteen types of base pairing, or the like. Complementary compounds of the invention may also contain pendent groups or moieties, either as part of or separate from the basic repeat unit of the polymer, to enhance specificity, nuclease resistance, delivery, or other property related to efficacy, e.g. cholesterol moieties, duplex intercalators such as acridine, poly-L-lysine, "end capping" with one or more nuclease-resistant linkage groups such as phosphorothioate, and the like. Sequences of certain representative oligonucleotides useful in this invention are set forth in the Sequence Listing.

Preferably, the oligonucleotide of the invention contains a modified internucleoside phosphate backbone to improve the bioavailability and hybridization properties of the oligonucleotide. Linkages are selected from the group consisting of phosphodiester, phosphotriester, methylphosphonate, phosphoroselenoate, phosphorodiselenoate, phosphoroanilothioate, phosphoroanilidate, phosphoramidate, phosphorothioate, phosphorodithioate or combinations thereof.

Preferably, nuclease resistance is conferred on the antisense compounds of invention by providing nuclease-resistant internucleosidic linkages. Many such linkages are known in the art, e.g. phosphorothioate: Zon and Geiser, *Anti-Cancer Drug Design*, 6:539–568 (1991); Stec et al, U.S. Pat. No. 5,151,510; Hirschbein, U.S. Pat. No. 5,166, 387; Bergot, U.S. Pat. No. 5,183,885; phosphorodithioates: Marshall et al, *Science*, 259:1564–1570 (1993); Caruthers and Nielsen, International application PCT/US89/02293; phosphoramidates, e.g.—OP(=O)(NR$^1$R$^2$)—O— with R$^1$ and R$^2$ hydrogen or $C_1$–$C_3$ alkyl: Jager et al, *Biochemistry*, 27:7237–7246 (1988); Froegler et al, International application PCT/US90/03138; peptide nucleic acids: Nielsen et al, *Anti-cancer Drug Design*, 8:53–63 (1993), International application PCT/EP92/01220; methylphosphonates: Miller et al, U.S. Pat. No. 4,507,433, Ts'o et al, U.S. Pat. No. 4,469,863, Miller et al, U.S. Pat. No. 4,757,055; and P-chiral linkages of various types, especially phosphorothioates, Stec et al, European patent application 92301950.9 and Lesnikowski, *Bioorganic Chemistry*, 21:127–155 (1993). Additional nuclease linkages include alkylphosphotriester such methyl- and ethylphosphotriester, carbonate such as carboxymethyl ester, carbamate, morpholino carbamate, 3'-thioformacetal, silyl such as dialkyl ($C_1$–$C_6$)- or diphenylsilyl, sulfamate ester, and the like. Such linkages and methods for introducing them into oligonucleotides are described in many references, e.g. reviewed generally by Peyman and Ulmann, *Chemical Reviews*, 90:1543–584 (1990); Milligan et al, *J. Med. Chem.*, 36:1923–1937 (1993); Matteucci et al, International application PCT/US91/06855. Preferably, phosphorus analogs of the phosphodiester linkage are employed in the compounds of the invention, such as phosphorothioate, phosphorodithioate, phosphoramidate, or methylphosphonate. More preferably, phosphorothioate is employed as the nuclease resistant linkage. It is understood that in addition to the preferred linkage groups, compounds of the invention may comprise additional modifications, e.g. boronated bases, Spielvogel et al, U.S. Pat. No. 5,130,302; cholesterol moieties, Shea et al, *Nucleic Acids Research*, 18:3777–3783 (1990) or Letsinger et al, *Proc. Natl. Acad. Sci.*, 86:6553–6556 (1989); 5-propenyl modification of pyrimidines, Froehler et al, *Tetrahedron Lett.*, 33:5307–5310 (1992); and the like. Preferred linkages also include N3'→P5' phosphoramidate linkages as described in PCT/US95/03575 application filed Mar. 20, 1995, and herein incorporated by reference.

Preferably, complementary compounds of the invention are synthesized by conventional means on commercially available automated DNA synthesizers, e.g. an Applied Biosystems (Foster City, Calif.) model 380B, 392 or 394 DNA/RNA synthesizer. Preferably, phosphoramidite chemistry is employed, e.g. as disclosed in the following references: Beaucage and Iyer, *Tetrahedron*, 48:2223–2311 (1992); Molko et al, U.S. Pat. No. 4,980,460; Koster et al, U.S. Pat. No. 4,725,677; Caruthers et al, U.S. Pat. Nos. 4,415,732; 4,458,066; and 4,973,679; and the like.

The length of an oligonucleotide is sufficiently large to ensure that specific binding will take place only at the desired target polynucleotide and not at other fortuitous sites, as explained in many references, e.g. Rosenberg et al, International application PCT/US92/05305; or Szostak et al, *Meth. Enzymol.* 68:419–429 (1979). The upper range of the length is determined by several factors, including the inconvenience and expense of synthesizing and purifying oligomers greater than about 30–40 nucleotides in length, the greater tolerance of longer oligonucleotides for mismatches than shorter oligonucleotides, whether modifications to enhance binding or specificity are present, whether duplex or triplex binding is desired, and the like. Usually, complementary compounds of the invention have lengths in the range of about 12 to 60 nucleotides. More preferably, complementary compounds of the invention have lengths in the range of about 15 to 40 nucleotides; and most preferably, they have lengths in the range of about 18 to 30 nucleotides. A preferred aspect is a phosphorothioate oligodeoxynucleotide ("(S)ODN") having the nucleic acid sequence 5'-AACGTTGAGGGGCAT-3', SEQ. ID NO.: 1.

Preferably, the thermal stability of the complementary oligonucleotides of the invention are determined by way of melting, or strand dissociation, curves. The temperature of fifty percent strand dissociation is taken as the melting temperature, $T_m$, which, in turn, provides a convenient measure of stability. $T_m$ measurements are typically carried out in a saline solution at neutral pH with target and complementary oligonucleotide concentrations at between about 1.0 and 2.0 $\mu$M. Typical conditions are as follows: 150 mM NaCl and 10 mM $MgCl_2$ in a 10 mM sodium phosphate buffer (pH 7.0) or in a 10 mM tris-HCl buffer (pH 7.0); or like conditions. Data for melting curves are accumulated by heating a sample of the complementary oligonucleotide/target polynucleotide complex from room temperature to about 85–90° C. As the temperature of the sample increases, absorbance of 260 nm light is monitored at 1° C. intervals, e.g. using a Cary (Australia) model 1E or a Hewlett-Packard (Palo Alto, Calif.) model HP 8459 UV/VIS spectrophotometer and model HP 89100A temperature controller, or like instruments. Such techniques provide a convenient means for measuring and comparing the binding strengths of complementary oligonucleotides of different lengths and compositions.

In embodiments where triplex formation is desired, there are constraints on the selection of target sequences. Generally, third strand association via Hoogsteen type of binding is most stable along homopyrimidine-homopurine tracks in a double stranded target. Usually, base triplets form in T-A*T or C-G*C motifs (where "-" indicates Watson-Crick pairing and "*" indicates Hoogsteen type of binding); however, other motifs are also possible. For example, Hoogsteen base pairing permits parallel and antiparallel orientations between the third strand (the Hoogsteen strand) and the purine-rich strand of the duplex to which the third strand binds, depending on conditions and the composition of the strands. There is extensive guidance in the literature for selecting appropriate sequences, orientation, conditions, nucleoside type (e.g. whether ribose or deoxyribose nucleosides are employed), base modifications (e.g. methylated cytosine, and the like) in order to maximize, or otherwise regulate, triplex stability as desired in particular embodiments, e.g. Roberts et al, *Proc. Natl. Acad. Sci. USA*, 88:9397–9401 (1991); Roberts et al, *Science*, 258:1463–1466 (1992); Distefano et al, *Proc. Natl. Acad. Sci. USA*, 90:1179–1183 (1993); Mergny et al, *Biochemistry*, 30:9791–9798 (1991); Cheng et al, *J. Am. Chem. Soc.*, 114:4465–4474 (1992); Beal and Dervan, *Nucleic Acids Research*, 20:2773–2776 (1992); Beal and Dervan, *J. Am. Chem. Soc.*, 114:4976–4982 (1992); Giovannangeli et al, *Proc. Natl. Acad. Sci. USA*, 89:8631–8635 (1992); Moser and Dervan, *Science*, 238:645–650 (1987); McShan et al, *J. Biol. Chem.*, 267:5712–5721 (1992); Yoon et al, *Proc. Natl. Acad. Sci. USA*, 89:3840–3844 (1992); Blume et al, *Nucleic Acids Research*, 20:1777–1784 (1992); and the like.

Inhibition of Melanoma Cancer Cell Proliferation

Figure 1B:
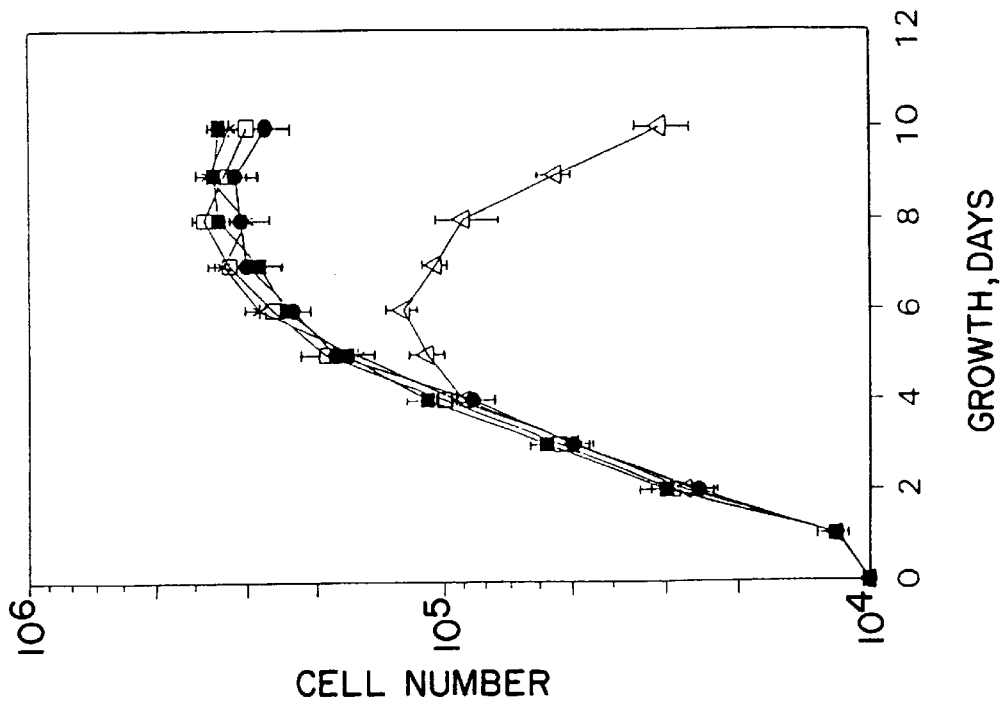
FIGS. 1A–C shows the proliferation of melanoma cells. M14 (panel A), JR8 (panel B) and PLF2 (panel C) melanoma cells after exposure to c-myc (S)ODNs ("(S)ODNs") for 4 days, starting from day 1 after seeding. Cells are treated with 100 µg/ml on day 1 and with 50 µg/ml on days 2 up to 4. Each point represents the mean ±SD of triplicate samples. All experiments were repeated at least twice. Figure symbols refer to (•) untreated, (Δ) antisense-, (□) scrambled-, (■) "G-quartet"- and (*) sense-treated cells.
Figure 1A:
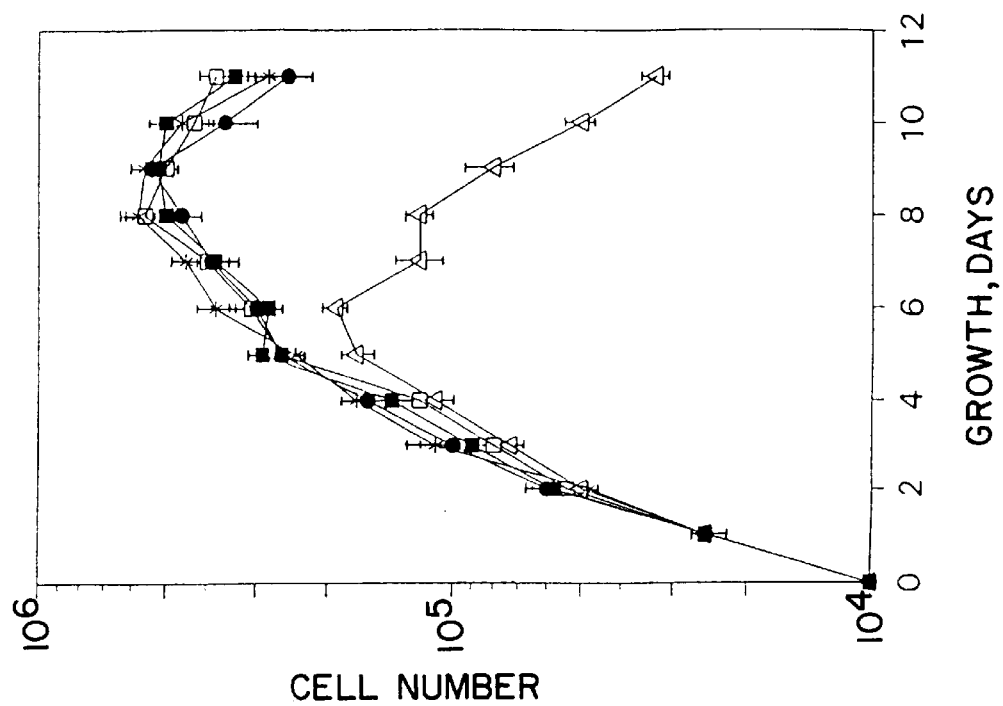
Figure 1C:
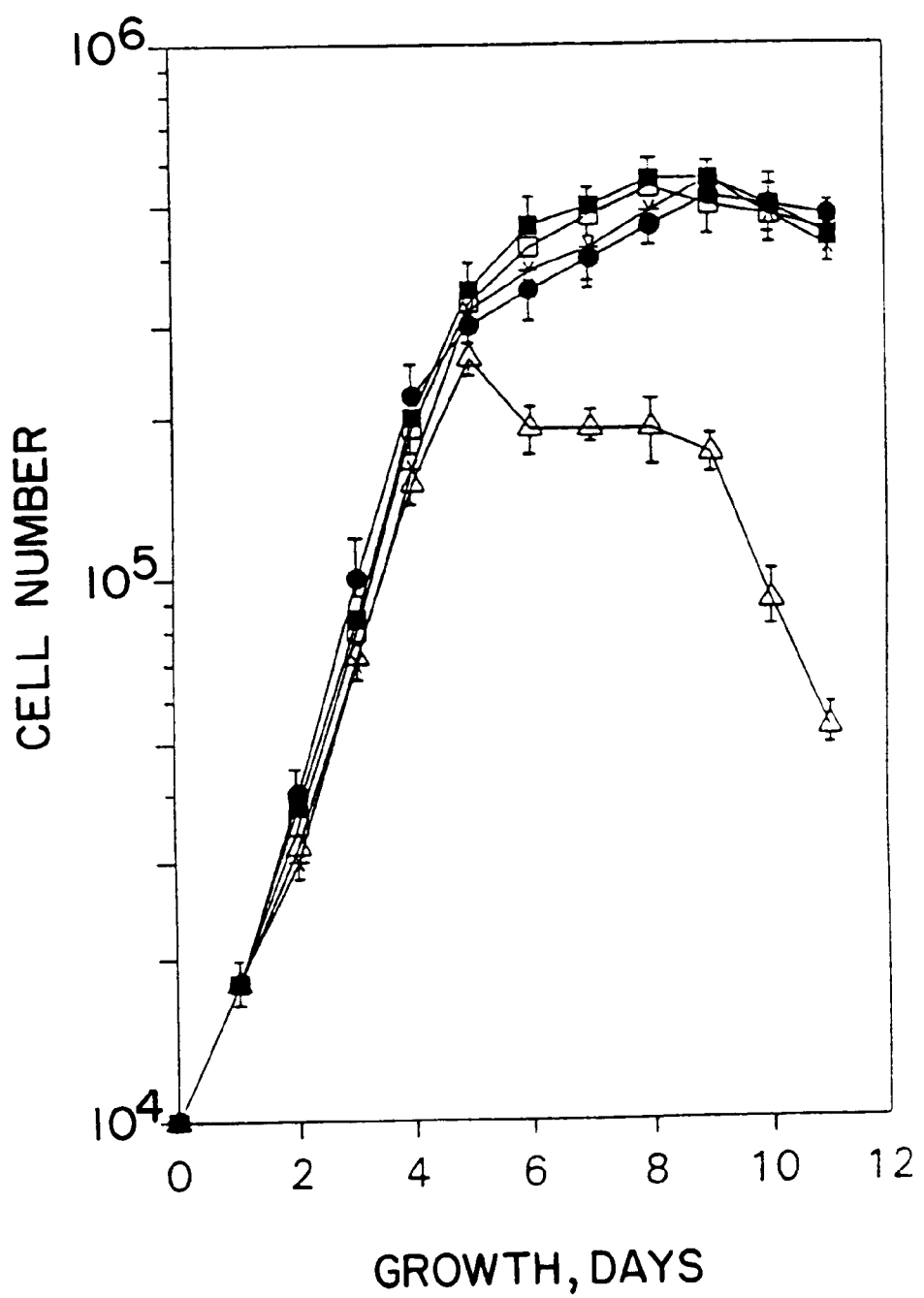

The oligonucleotides, such as ODNs, of the present invention are effective inhibitors of human melanoma tumor growth in vitro, as well as in vivo. The exposure of melanoma cells in vitro to (S)ODNs complementary to c-myc mRNA (c-myc (S)ODNs) results in a significant inhibition of cell proliferation clearly evident by day 6 of cell growth, but already detectable by day 4 (FIG. 1). To demonstrate the specificity of c-myc (S)ODN: c-myc mRNA interaction, three different controls are used, i.e., one sense and two scrambled sequences. In particular, since the c-myc (S)ODNs contained four contiguous guanosine residues (the "G-quartet"), postulated to inhibit proliferation nonspecifically (Yaswen et al., *Antisense Res Dev* 3:67–77 (1993)), one of the control (S)ODNs contains a scrambled sequence with the "G-quartet". The results show that the scrambled "G-quartet" (S)ODNs did not affect proliferation of the melanoma cell lines. The selective activity of the c-myc (S)ODN sequence is also supported by the early decrease in c-myc expression, which is detectable by 24 hours after exposure to c-myc (S)ODNs, with a further decrease after 72 hours, but with no change in viable cell number. Thus, the decrease in melanoma cell proliferation after treatment with c-myc (S)ODNs is specific for oligonucleotides of the invention.

Treatment with (S)ODNs complementary to c-myc mRNA induces a down-regulation of c-myc expression, followed by an inhibition of cell proliferation. The inhibition of cell proliferation is followed by a decrease in cell viability as reflected, at least in part, by the appearance of cells with a hypodiploid DNA content, as described in the examples. Such observations are consistent with induction of apoptosis by c-myc oligonucleotide treatments.

In cells arising from a solid tumor expressing c-myc, the continuous suppression of endogenous c-myc is directly involved in the inhibition of cellular proliferation and in the induction of programmed cell death of melanoma cancer cells. Therefore, the oligonucleotides of the invention are effective for killing melanoma cells and one mechanism for cell death is the induction of apoptosis. The in vitro results with a newly explanted (1st in vitro passage) human melanoma cells (NG) confirm the antiproliferative effect of (S)ODNs complementary to c-myc mRNA, which reduces the percentage of the NG cell population in S-phase of the cell cycle.

Figure 3A:
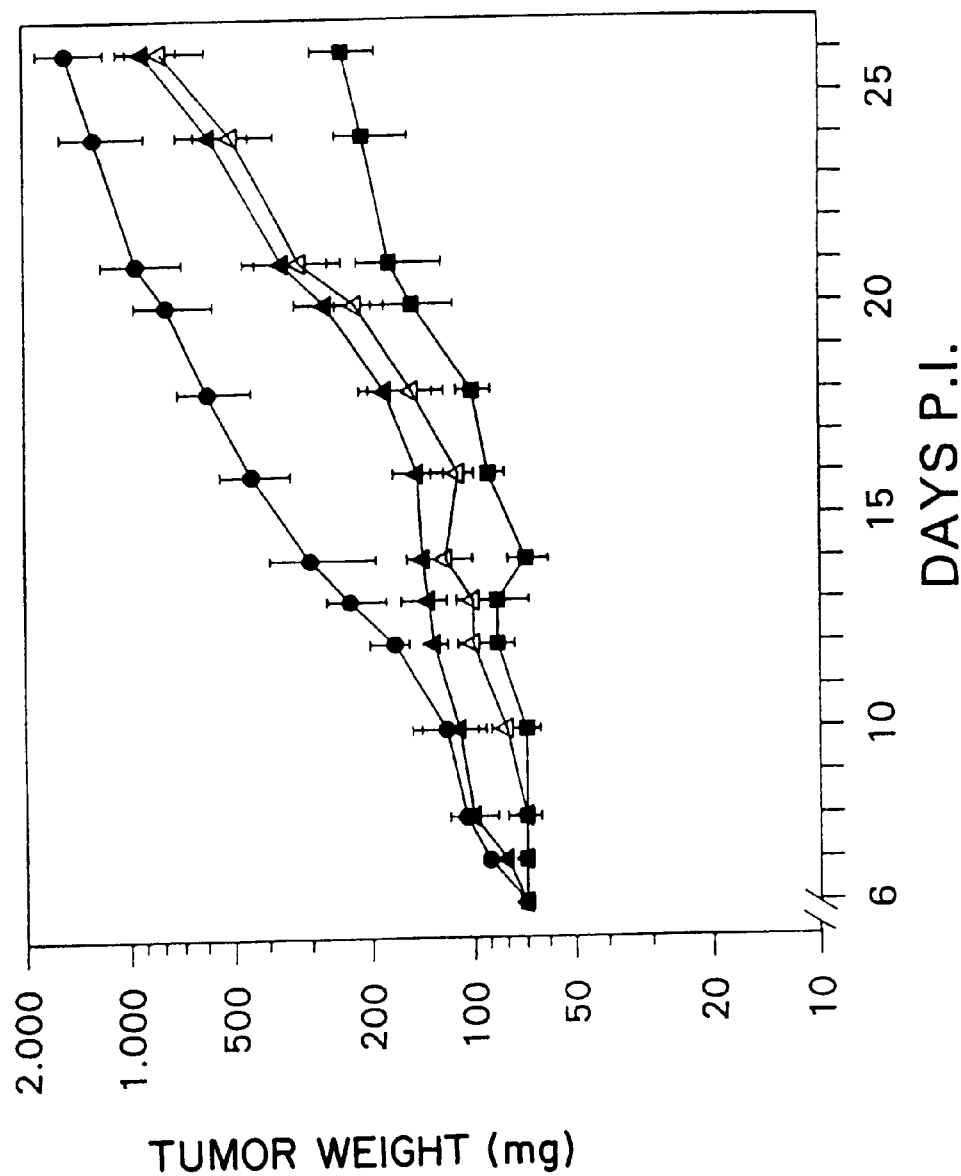
FIGS. 3A–C shows the effect of different administration schedules of intravenously administered (S)ODNs on the growth of NG tumor implanted in nude mice. In each experiment, treatment starts on day 1 after tumor implantation. Panel A: animals are treated with EBSS ("Earle's Balanced Salt Solution") (control group; ●) or c-myc (S)ODNs 0.25 mg/mouse/day (n=8; ▲); 0.5 mg/mouse/day (n=8; Δ); 1 mg/mouse/day (n=8; ■). Tumor growth in mice treated with scrambled (S)ODNs, using the same schedules as for antisense (S)ODNs, do not differ from that of untreated mice. Panel B: animals are treated with EBSS or c-myc (S)ODNs for 8 consecutive days as follows: EBSS/mouse/day (n=10; •); c-myc (S)ODNs 0.25 mg/mouse/day (n=9; □); 0.5 mg/mouse/day (n=20; ○); 0.25 mg/mouse/day scrambled (n=8; ■); 0.5 mg/mouse/day scrambled (n=17; Δ). A second cycle of treatment was started after a 7-day interval. Panel C: animals are treated with EBSS or 1 mg of c-myc (S)ODNs on days 1, 3, 5, and 7 and 0.5 mg of c-myc (S)ODNs on days 2, 4, 6, and 8. A second cycle of treatment was started after a 6-day interval. Schedules: EBSS (n=10; •); c-myc (S)ODNs (n=8; □); scrambled (n=8; Δ). Each point represents the mean ±SD. Slopes of the tumor growth curves in each panel and of the curves obtained for the scrambled (S)ODNs treated tumors not included in panel A were determined and given below.
Figure 3B:
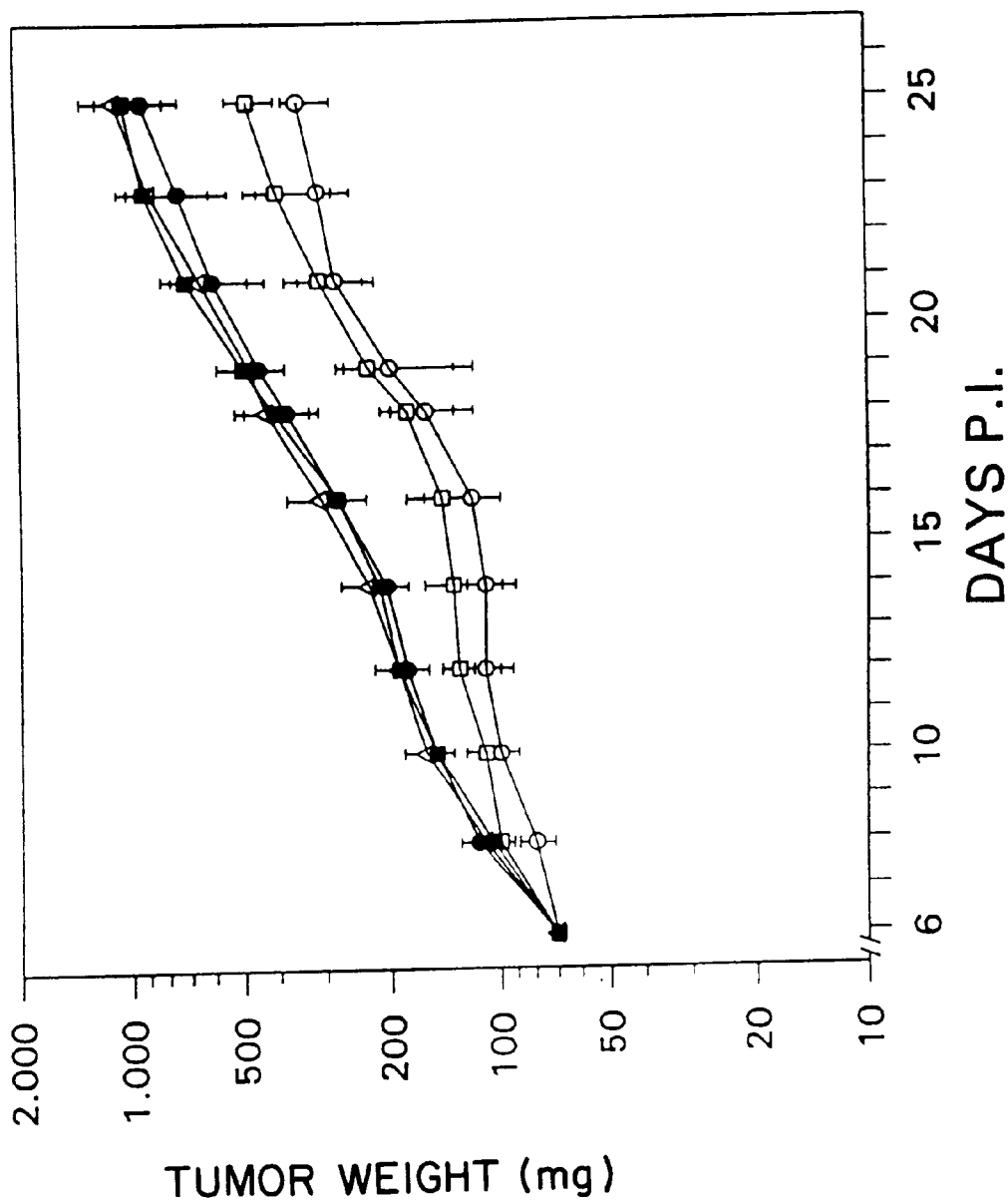
Figure 3C:
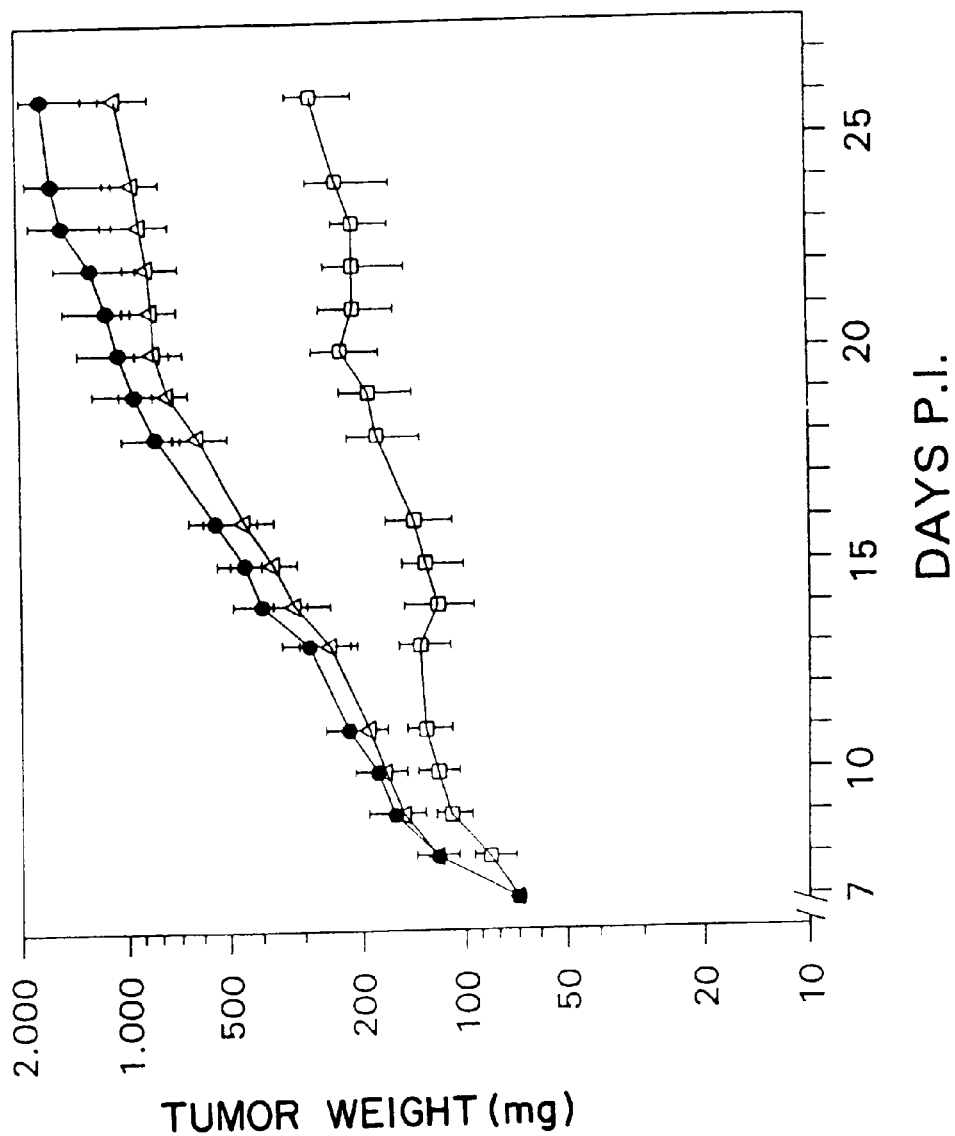

Melanoma tumor growth in vivo is also inhibited by c-myc oligonucleotide treatments. The dose-response relationship and the absence of an antitumor effect of the sense and scrambled (S)ODN controls, demonstrate that (S)ODNs complementary to c-myc mRNA are responsible for the antitumor activity observed in Example 8 (FIGS. 3A, 3B, 3C). Down-regulation of c-myc levels in NG tumors after in vivo c-myc (S)ODN treatment is also sequence specific (FIG. 4). Moreover, the decrease in c-myc expression was also observed as early as 24 hours after treatment with a single bolus, when the antitumor effect was not yet evident, thereby confirming that the decreased c-myc expression was specifically related to treatment with (S)ODNs complementary to c-myc mRNA. In vivo experiments also revealed programmed cell death in tumors from mice treated with c-myc (S)ODNs as compared with tumors from untreated or scrambled-treated mice.

One aspect of the invention includes a method of inhibiting proliferation of human melanoma cancer cells. Human melanoma cancer cells are contacted with a c-myc oligonucleotide in an amount sufficient to inhibit proliferation. The c-myc oligonucleotide is complementary to a nucleotide sequence of human c-myc mRNA and is usually at least 10 bases in length. Generally, c-myc oligonucleotides inhibit proliferation of cultured human melanoma cells by at least 10%, preferably at least 50% and more preferably at least 75%, at a concentration of 10 $\mu$M compared to proliferation of cultured human melanoma cells in the absence of c-myc oligonucleotide. Usually, the human melanoma cells are cultured in the presence of serum at 37° C. for these type of activity assays. Contacting a c-myc oligonucleotide to human melanoma cancer cells will also kill the cells or induce apoptosis. Human melanoma cancer cells can form tumors and can comprise tumors of the skin of variable mass, such as from 0.2 to 50 g, though tumors are often in the 1 to 10 g range. Contacting melanoma cancer cells with c-myc oligonucleotides will also inhibit tumor formation.

Another aspect of the invention includes a method of decreasing the chemoresistance of melanoma cancer cells to cisplatin compound. Human melanoma cancer cells are contacted with a c-myc oligonucleotide in an amount sufficient to inhibit proliferation either before or after contacting the cells with cisplatin. Preferably, c-myc oligonucleotides are administered after the administration of cisplatin.

A preferred aspect is a method of inhibiting human melanoma tumor growth by administering to a patient in need thereof oligonucleotides of the invention. Such oligonucleotides will inhibit expression of c-myc protein, which is required for melanoma cancer cell survival. Oligonucleotides designed to bind nucleic acid of c-myc, can effect cell death by inducing apoptosis in the melanoma cancer cell. Such oligonucleotides also 1) inhibit metastasis and 2) promote the regression of a melanoma tumor (e.g. such as reduction in tumor mass). Tumor growth can be inhibited by administering a c-myc oligonucleotide that inhibits melanoma cell proliferation or triggers melanoma cell death. Likewise, tumor regression can be promoted by inducing melanoma cell death. Generally, c-myc oligonucleotides that are administered to a patient inhibit proliferation of cultured human melanoma cells by at least 10%, preferably at least 50% and more preferably at least 75%, at a concentration of 10 $\mu$M compared to proliferation of cultured human melanoma cells in the absence of c-myc oligonucleotide.

For inhibiting tumor growth, c-myc oligonucleotides can be administered by topically applying or by non-systemically injecting the c-myc oligonucleotide or cisplatin. If tumor requires surgical intervention, oligonucleotides can be applied before and after surgical removal of the human melanoma tumor. Administration can also comprise systemically injecting the c-myc oligonucleotide and the cisplatin compound.

For in vivo use, c-myc oligonucleotides may be combined with a pharmaceutically acceptable carrier, such as suitable liquid vehicle or excipient and an optional auxiliary additive or additives. Components of pharmaceutical compositions of the invention depend on several factors, including the nature of the disease or condition being treated, the location of disease lesions, the mode of drug delivery and/or administration contemplated, the latter of which can include in vivo administration by way of a catheter into a target lesion or organ, topical application, intranasal administration, administration by implanted or transdermal sustained release systems, and the like.

The present invention is also directed to methods of treating melanoma in mammals, comprising contacting the mammal with an effective amount of an ODN complementary to c-myc mRNA. Mammals include, but are not limited to the Order Rodentia, such as mice; Order Logomorpha, such as rabbits; more particularly the Order Carnivora, including Felines (cats) and Canines (dogs); even more particularly the Order Artiodactyla, Bovines (cows) and Suines (pigs); and the Order Perissodactyla, including Equines (horses); and most particularly the Order Primates, Ceboids and Simoids (monkeys) and Anthropoids (humans and apes). The mammals of most preferred embodiments are humans.

Pharmaceutical Compositions

Pharmaceutical compositions of the invention include c-myc oligonucleotides and a pharmaceutical carrier that may contain a variety of components that provide a variety of functions, including regulation of drug concentration, regulation of solubility, chemical stabilization, regulation of viscosity, absorption enhancement, regulation of pH, and the like. For example, in water soluble formulations the pharmaceutical composition preferably includes a buffer such as a phosphate buffer, or other organic acid salt, preferably at a pH of between about 7 and 8. For formulations containing weakly soluble oligonucleotide compounds, microemulsions may be employed, for example by using a nonionic surfactant such as Tween 80 in an amount of 0.04–0.05% (w/v), to increase solubility. Other components may include antioxidants, such as ascorbic acid, hydrophilic polymers, such as, monosaccharides, disaccharides, and other carbohydrates including cellulose or its derivatives, dextrins, chelating agents, such as EDTA, and like components well known to those in the pharmaceutical sciences, e.g. *Remington's Pharmaceutical Science,* latest edition (Mack Publishing Company, Easton, Pa.).

Complementary compounds of the invention include the pharmaceutically acceptable salts thereof, including those of alkaline earths, e.g. sodium or magnesium, ammonium or $NX_4^+$, wherein X is $C_1$–$C_4$ alkyl. Other pharmaceutically acceptable salts include organic carboxylic acids such as acetic, lactic, tartaric, malic, isethionic, lactobionic, and succinic acids; organic sulfonic acids such as methanesulfonic, ethanesulfonic, and benzenesulfonic; and inorganic acids such as hydrochloric, sulfuric, phosphoric, and sulfamic acids. Pharmaceutically acceptable salts of a compound having a hydroxyl group include the anion of such compound in combination with a suitable cation such as $Na^+$, $NH_4^+$, or the like.

Sustained release systems suitable for use with the pharmaceutical compositions of the invention include semipermeable polymer matrices in the form of films, microcapsules, or the like, comprising polylactides, copolymers of L-glutamic acid and gamma-ethyl-L-glutamate, poly(2-hydroxyethyl methacrylate), and like materials, e.g. Rosenberg et al, International application PCT/US92/05305. Sustained release systems also include liposomally entrapped complementary compounds, e.g. as described in Liposome Technology, Vol. II, *Incorporation of Drugs, Proteins and Genetic Material* (CRC Press). The oligonucleotide, depending upon its solubility, may be present in the aqueous layer or the lipidic layer, or in what is generally termed a liposomic suspension. The hydrophobic layer usually comprises phospholipids such as lecithin and sphintgomyelin, steroids such as cholesterol, ionic surfactants such as diacetylphosphate, stearylamine, or phosphatidic acid, and/or other such hydrophobic molecules. For example, oligonucleotides have been successfully encapsulated in unilamellar liposomes. Reconstituted Sendai virus envelopes have been successfully used to deliver RNA and DNA to cells (Arad et al., *Biochem. Biophy. Acta.,* 859:88–94 (1986)).

The oligonucleotide component of the therapeutic combination can be conjugated to poly(L-lysine) to increase cell penetration. Such conjugates are described by Lemaiture et al., *Proc. Natl. Acad. Sci. USA,* 84:648–652 (1987), provided that this is a ribonucleotide. The resulting aldehyde groups are randomly coupled to the epsilon-amino groups of lysine residues of poly(L-lysine) by Schiff base formation, and reduced with sodium cyanoborohydride, thereby converting the 3'-termination ribose ring into a morpholine structure.

The oligonucleotide can also be conjugated for therapeutic administration to ligand-binding molecules that recognize cell-surface molecules, examples of which are provided in International Patent Application WO 91/04753. In particular, transferrin-polylysine-oligonucleotide complexes can be preferred for uptake by cells expressing high levels of transferring receptor. The preparation of such complexes as carriers of oligonucleotide uptake into cells is described by Wagner et al., *Proc. Natl. Acad. Sci. USA,* 87:3410–3414 (1990). Inhibition of leukemia cell proliferation by transferrin receptor-mediated update of c-myc complementary oligonucleotides conjugated to transferrin has been demonstrated (Citro et al., *Proc. Natl. Acad. Sci. USA,* 89:70331–7035 (1992)).

An effective amount of c-myc oligonucleotide for particular applications depends on several factors, including the chemical nature of the oligonucleotide, the method of administration, and the like. Preferably, an effective amount will provide a concentration of c-myc oligonucleotide of between about 1 to 100 $\mu$M at the target polynucleotide; and more preferably, an effective amount will provide a concentration of oligonucleotide of between about 1 to 10 $\mu$M at the target polynucleotide.

Oligonucleotide Administration

The efficacy of c-myc oligonucleotides can be enhanced by varying the dosage and schedule of administration. Administration can be optimized as described herein in vivo modes and known in the art. For example, the NG tumor cells are injected into nude mice and used for in vivo experiments, in which the efficacy of (S)ODNs complementary to c-myc mRNA is evaluated not only in terms of tumor growth inhibition, but also in terms of reduction in the number of metastases and increase in lifespan. This last parameter represents a principal end-point in establishing the antitumor activity of a new drug. The therapeutic index of c-myc (S)ODNs can be enhanced by the schedule of administration, such as in Example 9.

Methods of administering the ODNs of the present invention include techniques well known in the art such as and not limited to liposomes, plasmid expression, retroviral vectors, splicing an oligonucleotide to another sequence such as a promoter or a growth factor, wherein the plasmid and/or vector is transfected with an expression plasmid expressing the ODN, exposing cells to a medium or wash containing the oligonucleotide. In the administration of oligonucleotides via vectors or plasmids, a non-coding RNA strand of c-myc is preferably used in order to produce RNA oligonucleotides complementary to c-myc which are expressed by the cell. The RNA oligonucleotides then bind c-myc coding RNA sequence.

Methods of administering the oligonucleotides to mammals include liposomes, and may be in a mixture with a pharmaceutically-acceptable carrier, selected with regard to the intended route of administration and the standard pharmaceutical practice. In addition, antibodies, ligands and the like may be incorporated in to the liposomes thereby providing various modes of inhibiting c-myc at the same time. Dosages will be set with regard to weight, and clinical condition of the patient. The proportional ratio of active ingredient to carrier will naturally depend on the chemical nature, solubility, and stability of the compounds, as well as the dosage contemplated. Generally, per day systemic dosages can vary from 0.1 to 1,000 mg for humans and preferably from 10 to 400 mg and more preferably from 10 to 200 mg. Generally, per day per kg dosages can vary 0.1 mg to 15 mg and preferably from 0.6 mg to 6.0 mg. The oligonucleotides of the present invention will be administered for a time sufficient to reduce tumor weight and delay tumor regrowth. As shown in Example 9, the therapeutic efficacy of (S)ODNs complementary to c-myc mRNA can be maximized by varing dose and schedule. For example, a significant reduction in the number of lung metastases can be observed, accompanied by a significant increase in animal survival by alternating dosages. In particular, alternate doses of 1 mg and 0.5 mg for 8 consecutive days, repeated after a 7-day interval, reduced tumor weight by approximately 80% and delayed tumor regrowth by 16 days. Treatment with scrambled or "G-quartet" scrambled (S)ODNs had no effect on tumor growth. Thus, c-myc oligonucleotide administration effectively inhibits metastasis and tumor growth, and can promote tumor regression.

The oligonucleotides of the invention may be employed in the method of the invention either singly or in combination with other compounds used in cancer therapy. One preferred such compound is cisplatin, which can be co-administered or administered sequentially. The non-oligonucleotide agent can be administered through any of the routes recommended for such agents. Typically, the non-oligonucleotide agent will be administered parentally, such as through intravenous injection or infusion. The oligonucleotide and non-oligonucleotide agents can be administered simultaneously, such as in the form of an single pharmaceutical composition, or the two agents can be administered separately, in sequence. The administration protocol will vary according to the properties of the non-oligonucleotide agent and the sites in the organism to which the compounds are to be delivered. Appropriate dosages for the non-oligonucleotide agent can be determined based on standard clinical usage. Preferably, cisplatin is administered first, followed by the ODNs of the invention. The amount to be administered will also depend on such factors as the age, weight, and clinical condition of the patient. See Gennaro, Alfonso, ed., *Remington's Pharmaceutical Sciences*, 18th Edition, 1990, Mack Publishing Co., Easton Pa. For cisplatin administration to patients, melanoma cancer cells or tumors are treated with cisplatin in combination with c-myc oligonucleotide by administering 1 to 20 mg/m$^2$ IV ("intravenous") daily for 1 to 5 days. Alternatively, higher amounts such as 100 mg/m$^2$ IV once every four weeks can be used. Generally, pretreatment hydration is recommended 8 to 12 hours prior to treatment with cisplatin. Cisplatin can also be intraperitoneally injected. Care must be taken that the cisplatin not come into contact with aluminum as this could result in precipitate formation and a loss of potency. Because cisplatin treatment produces cumulative nephrotoxicity, cisplatin should generally not be given more frequently than once every 3 to 4 weeks. Subsequent doses of cisplatin should generally not be given until the serum creatinine is below 1.5 mg/100 ml and/or the BUN is below 25 mg/100 ml and audiometric analysis indicates that auditory acuity is within normal limits.

The compounds of the present invention may be administered by any suitable route, including inoculation and injection, for example, intravenous, oral, intraperitoneal, intramuscular, subcutaneous, topically, and by absorption through epithelial or mucocutaneous linings, for example, nasal, oral, vaginal, rectal and gastrointestinal.

The mode of administration of the oligonucleotides may determine the sites in the organism to which the compound will be delivered. For instance, topical application may be administered in creams, ointments, gels, oils, emulsions, pastes, lotions, and the like. The oligonucleotides of the present invention may be administered alone or will generally be administered in admixture with a pharmaceutical carrier selected with regard to the intended route of administration and standard pharmaceutical practice.

For topical application in the treatment of melanoma or in the prevention of metastasis following surgical removal of a melanoma, the administered dose (amount of oligonucleotide agent applied to tissue) will generally range from 0.01 μg to 10 mg of drug per cm$^2$, preferably from 0.2 μg to 7 mg of oligonucleotide per cm$^2$, and more preferably from 0.5 to 4 mg of oligonucleotide per cm$^2$. These dosages can be used on a per day basis. Administered dose for use with post-surgical dressing is preferably from 0.2 mg to 4 mg of oligonucleotide per cm$^2$. The administered dose for use with topical creams for post-surgical treatments is preferably from 0.05 mg to 3 mg of oligonucleotide per cm$^2$. For parenteral administration, most preferably intravenous administration, the oligonucleotides agents and non-oligonucleotide agents are best used in the form of sterile aqueous solution which may contain other solutes, for example, sufficient salts, glucose or dextrose to make the solution isotonic. For oral mode of administration, the present invention may be used in the form of tablets, capsules, lozenges, troches, powders, syrups, elixirs, aqueous solutions and suspension, and the like. Various disintegrants such as starch, and lubricating agents may be used. For oral administration in capsule form, useful diluents are lactose and high molecular weight polyethylene glycols. When aqueous suspensions are required for oral use, certain sweetening and/or flavoring agents may be added.

EXAMPLES

Example 1

Synthesis of Stable Oligodeoxynucleotides

The rapid degradation oligodeoxynucleotides (ODNs) with naturally occurring phosphodiester linkages by various enzymes possessing nucleolytic activities that are present both inside and outside of cells can be improved by introducing nucloase-resistance internucleoside linkages into the oligonucleotide (Eder et al., *Antisense Res Dev* i:141–151 (1991); Dagle et al., *Antisense Res Dev* 1:11–20 (1991); Wickstrom et al., *J Biochem Biophys Methods* 13:97–102 (1987)). ODNs with modified intenucleoside phosphate backbones, such as phosphorothioates ("(S) ODNs"), have been developed, and they are more resistant to nuclease degradation than their unmodified counterparts (Stein et al., *Nucleic Acid Res* 16:3209–3221 (1988); Agrawal et al., *Proc Natl Acad Sci USA* 88:7595–7599 (1991)). Other internucleoside linkages, such N3'→P3 phosphoramidate linkages, can be used as well. Additional methods for synthesizing oligonucleotides containing N3'→P5' phosphoramidate linkages or alternating phosphoramidate linkages are disclosed in PCT patent application PCT/US95/03575 and are herein incorporated by reference.

c-myc Oligonucleotide Sequences

Oligonucleotides with different nucleotide sequences can be synthesized and conveniently tested for activity using the assays described herein. For a 15-mer oligodeoxynucleotide (S)ODNs (5'-AACGTTGAGGGGCAT-3') (SEQ ID NO.: 1) complementary to the translation initiation region of c-myc mRNA can be used. Other c-myc oligonucleotides can also be selected and used in the methods described, for example the c-myc oligonucleotides described in Table 1. As controls, a sense (5'-ATGCCCCTCAACGTT-3') (SEQ ID NO.: 2) and two scrambled (5'-AACGTGGATTGGCAG-3' (SEQ ID NO.: 3) and 5'-AAGCATACGGGGTGT-3') (SEQ ID NO.: 4) (S)ODNs are used in different experiments. The second scrambled sequence contains the "G quartet" motif and is referred to throughout the text as "G quartet"-scrambled (S)ODN. (S)ODNs can be prepared, purified, and dried under vacuum. (S)ODNs are resuspended in sterile Earle's balanced salts solution ("EBSS"), (BIO-Whittaker, Walkersville, USA). The nucleotide sequence of HSMYC/Gene Genebank Accession # V00568 is herein incorporated by reference.

TABLE 1

| SEQ ID NO. | Oligonucleotide Sequence (5'→3') | Human c-myc Nucleotide Location (HSmyc/Gene Acession # V00568); Oligonucleotide Type | |
|---|---|---|---|
| 1 | AACGTTGAGG GGCAT | 559–573 | Reverse Complement |
| 2 | ATGCCCCTCA ACGTT | 573–559 | Sense |
| 3 | AACGTGGATT GGCAG | | Mismatch SEQ ID No 1 |
| 4 | AAGCATACGG GGTGT | | Mismatch SEQ ID No 1 |
| 5 | AACGTTGAGG GGCAT | 559–573 | Reverse Complement |
| 6 | GGCCTTTTCA TTGTTTTCCA | 1709–1728 | Reverse Complement |
| 7 | AAAGTGCCCG CCCGCTGCTA | 358–377 | Reverse Complement |
| 8 | CCAGTGCAAA GTGCCCGCCC | 365–384 | Reverse Complement |
| 9 | GGGAGAGTCG CGTCCTTGCT | 400–419 | Reverse Complement |
| 10 | TCATGGAGCA CCAGGGGCTC | 1264–2383 | Reverse Complement |
| 11 | CGTTCTTTTT TCCCGCCAAG | 80–99 | Reverse Complement |
| 12 | CATTGTTTTC CAACTCC | 1704–1720 | Reverse Complement |
| 13 | TGATGGAGCA CCAGGGGCTC | | Mismatch SEQ ID No 1 |
| 14 | GAGCACCAGG GGCTC | 1264–1278 | Reverse Complement |
| 15 | GGAGCACCAG GGGCT | 1265–1279 | Reverse Complement |
| 16 | TGGAGCACCA GGGGC | 1266–1280 | Reverse Complement |
| 17 | ATGGAGCACC AGGGG | 1264–1281 | Reverse Complement |

Example 2

Melanoma Cell Line Cell Culture and Tumor Implantation Methods

Melanoma Cell Culture.

Three previously characterized human melanoma cell lines (M14, JR8 and PLF2) (Greco et al., *Anticancer Res* 7:839–844 (1987); Zupi et al., *Proc Am Assoc Cancer Res* 26:22 (1985)) are used for in vitro studies. The cells are maintained as monolayer cultures in RPMI-1640 supplemented with 10% fetal calf serum, penicillin/streptomycin and L-glutamine at 37° C. in a humidified incubator with a 5% $CO_2$ and 95% air atmosphere.

NG melanoma cultures are obtained using mechanical disaggregation (Greco et al., *Tumori* 65:169–180 (1979)) of tissue explants from human tumors grown in nude mice. All in vitro experiments with NG cultures are performed at the $1^{st}$ passage.

Table 2 summarizes cell types described in the cell culture experiments.

TABLE 2

| Established Human Melanoma Cell Lines | Source or Reference |
|---|---|
| M14 | Greco et al. 1987; Zupi et al. 1985 |
| JR8 | Greco et al. 1987; Zupi et al. 1985 |
| PLF2 | Greco et al. 1987; Zupi et al. 1985 |

TABLE 2-continued

| Primary Human Melanoma Cells | Source |
|---|---|
| NG | Human patient biopsy tumors grown in nude mice |

Tumor Implantation

A human primary melanoma (NG, V Clark's level), obtained from the biopsy of a patient is also employed for both in vitro and in vivo studies. The tumor, characterized immunohistochemically using specific MoAbs (HMB45 and Epi-3) that recognize human melanoma cells (Mottolese et al., *Melanoma Res.* 4:53–58 (1994)) is transplanted in nude mice after mechanical disaggregation of fragments of the biopsy material (Greco et al., *Tumori* 65:169–180 (1979)) with a cell viability of 60–70% as determined by the trypan-blue exclusion test. Solid tumors are obtained by injecting $2.5 \times 10^6$ viable cells into the hind leg muscles of CD-I male nude mice (nu/nu). Intramuscular implantation results in more homogeneous tumor growth than that obtained using subcutaneous implantation, with a 100% tumor take obtainable 4–5 days after introducing the implant. Spontaneous lung metastases are observable in all mice injected intramuscularly. All of the in vivo experiments are carried out at varying points between the $2^{nd}$ and the $8^{th}$ transplant.

Example 3 c-myc mRNA Levels are 5-to-9 Fold Higher in Human Melanoma Cells Compared to Normal Leukocytes To compare the mRNA levels in human melanoma cells and normal leukocytes, total RNA is extracted from melanoma cell cultures using the guanidium hydrochloride method (Chomczysky et al., Anal Biochem 162:156–159 (1987)). For Northern blot analysis, 30 μg of total RNA is separated in a 1% agarose gel containing 6.7% formaldehyde. RNA blotting and hybridization with radiolabeled probes (prepared by the random priming method (Feinberg et al., *Anal. Biochem.* 132:6 (1983)) are carried out by use of standard procedures (Sambrook J, Fritsch E F, Maniatis T: *Molecular cloning: a laboratory manual.* Cold Spring Harbor Laboratory, Cold Spring Harbor, N.Y. (1989)). Messenger RNA sizes are based on their migration in the gels relative to endogenous 28S and 18S ribosomal RNA. A c-myc probe containing the second and third exons of the mouse c-myc gene is used (Lombardi et al., Cell 49:161–170 (1987)). Northern blots are first hybridized with the c-myc probe and, after stripping (1 h at 80° C. in 10 mM Tris-1 mM EDTA, pH 8.0) reprobed with a 1.2-Kb Pst I fragment of the chicken glyceraldehyde-3-phosphate dehydrogenase (GAPDH) cDNA (Dugaiczyk et al., Biochemistry 22:1605–1613 (1983) obtainable from Dr. A. Felsani, (National Research Council Rome, Italy) to assess for equivalence of RNA loading and transfer.

Expression of c-myc mRNA is readily detected in the M14, JR8 and PLF2 cell lines and also in the primary (NG) melanoma culture, consistent with the reported expression of c-myc in melanoma cells, but not in normal melanocytes (Chenevix-Trench et al., *Oncogene* 5:1187–1193 (1990)). Compared to normal leukocytes, c-myc mRNA levels are 5-to-9-fold higher in melanoma, as indicated by densitometric analysis.

Example 4 c-myc Oligonucleotides Inhibit Proliferation of Established Human Melanoma Cell Lines To establish the ability of (S)ODNs complementary to c-myc mRNA (c-myc (S)ODNs) to inhibit proliferation of human melanoma cells, M14, JR8, and PLF2 cells are treated with equal doses of (S)ODNs complementary to the translation initiation region of c-myc mRNA for 4 days and assessed for their ability to continue proliferating.

To demonstrate the specificity of the effect of c-myc (S)ODNs, three different controls are used, i.e., one sense and two scrambled sequences. In particular, since this procedure uses (S)ODNs complementary to c-myc mRNA contain four contiguous guanosine residues (the "G-quartet"), postulated to inhibit proliferation nonspecifically (Yaswen et al., *Antisense Res Dev* 3:67–77 (1993)), one of the control (S)ODNs contains a scrambled sequence with the "G-quartet."

M14, JR8, and PLF2 cells are cultured in 24-well plates at a concentration of $10^4$ cells/well. After 24 hours, (S)ODNs are added at a concentration of 100 μg/mL, followed by doses of 50 μg/mL added at 48, 72, and 96 hours after seeding. Equimolar amounts of c-myc sense and two scrambled (S)ODNs are used in control experiments. Cell numbers and viability are determined daily using a Coulter Counter (model ZM, Kontron) and the trypan-blue exclusion test.

Treatment with (S)ODNs complementary to c-myc mRNA markedly inhibit growth of the cells of the three melanoma cell lines (>50%). This inhibition can be detected within 24 hours of the end of treatment (i.e., on day 5 of growth) (FIGS. 1A–C) and is clearly evident by day 6 of cell growth.

Example 5

Inhibition of Proliferation of a Newly Explanted Melanoma Primary Cell Line (NG)

To determine whether freshly explanted tumor cells are inhibited by c-myc oligonucleotides, human melanoma tumors from nude mice are isolated as explants and allowed to proliferate in vitro in the presence and absence of c-myc oligonucleotides. Results obtained with the established cell lines are predictive of the effect of c-myc antisense (S)ODNs on a newly explanted ($1^{st}$ in vitro passage) melanoma line (NG), as well as in vivo activity.

Cell cycle analysis of (S)ODN-treated NG cells

NG cultures growing in 24-well plates are exposed to (S)ODNs as described in Example 4. Cells are harvested on days 2, 3, 4, and 6 of growth, washed in PBS, and fixed with a solution of acetone-methanol (1:4, v/v) in 50% PBS at 4° C. for at least 30 minutes. Samples of $2 \times 10^5$ cells stained in a solution containing 75 KU/mL RNase and 50 μg/mL Propidium Iodide (PI) are analyzed in a FACScan cytofluorimeter (Becton Dickinson, San Jose, Calif., USA). Linear PI-red-fluorescence is monitored using an LP 620 filter. Twenty thousand events/sample are stored, and the histograms further analyzed to estimate the percentage of cells in various cell cycle phases, using a Becton Dickinson (San Jose, Calif., USA) software package.

Western blot and FACS analysis of c-myc in NG cells

Approximately $5 \times 10^5$ cells from NG cultures incubated with (S)ODNs are collected at the indicated times of treatment (8, 24, 72 hours) and then stored at −80° C. Frozen cell samples are solubilized in lysis buffer [0.01 M Tris-HCl (pH 7.5), 0.144 M NaCl, 0.5% NonidetP-40, 0.5% sodium dodecyl sulfate (SDS), 0.1% aprotinin, 10 μg/mL leupeptin, and 2 mM PMSF and sonicated. Protein samples are quantified using the BCA protein assay (Pierce, Rockford, Ill., USA). Thirty micrograms of protein/sample are subjected to SDS-polyacrylamide gel electrophoresis (4–15% acrylamide) (Laemmli UK *Nature* 227:681–685 (1970)), and pre-stained molecular weight markers (Amersham LIFE SCIENCE, Little Chalfont, UK) are used to locate the gel region containing the p62 c-myc protein. Following protein blotting to nitrocellulose membranes, an anti-human c-myc monoclonal antibody (MoAb) (clone 9E 10, Cambridge Research Biochemicals, London, UK) (Evan et al., *Mol Cell Biol* 5:3610–3616 (1985)) and an anti-human β-actin MoAb (clone JLA 20, Oncogene Science, NY, USA), are used simultaneously to localize c-myc and β-actin, respectively. β-actin serves as control for equivalence of protein transfer to membranes. Peroxidase-conjugated goat anti-mouse antibodies (Biorad Laboratories, Richmond, Calif., USA) are used as secondary antibodies. Immune complexes (i.e. proteins of interest) are visualized using an enhanced chemiluminescence system, (Amersham, UK) according to the manufacturer's instructions. Relative amounts of transferred c-myc protein are quantified by scanning densitometry and normalized against the amounts of β-actin present in the same sample.

FACS Results

The antiproliferative effect of c-myc antisense (S)ODNs on NG primary cultures is evaluated by FACS analysis and is based on the estimated percentage of cells in S-phase of the cell cycle. The c-myc antisense (S)ODN treatment induces a decrease in the proportion of cells in S-phase associated with a concomitant accumulation in the $G_0/G_1$ phases. This decrease in S-phase NG cells is apparent on day 3 of (S)ODN treatment (day 4 of growth; % S-phase ±SE=25±1, 26±1.5 and 18±2, in untreated, scrambled-, and antisense-treated cells, respectively). A further decrease in cell proliferation is observed at day 6 of growth (%S-phase ±SE=24±1.5, 24±1.5, and 10±2.1 in untreated, scrambled-, and antisense-treated cells, respectively).

Western Results

Expression of c-myc in the NG primary melanoma cells after (S)ODN treatment is examined by Western blot analysis. Immunoblot analysis of c-myc expression in lysates from untreated (C), scrambled-(S) and antisense-(AS) treated NG cells at various times after the beginning of (S)ODN treatment demonstrates that c-myc levels, normalized to β-actin levels, are reduced by 35, and 75% after 24, and 72 hours of antisense oligomer exposure, respectively. Treatment of the cells with the scrambled sequence induces no decrease in c-myc levels.

In sum, the in vitro results with NG confirm the antiproliferative effect of c-myc oligonucleotides, such as antisense (S)ODNs, which reduces the percentage of the NG cell population in S-phase of the cell cycle.

Example 6
c-myc Oligonucleotides Induce Apoptosis of Established Melanoma Cell Lines and Tumor Cells To determine the effect of (S)ODNs complementary to c-myc mRNA on the induction of apoptosis, apoptosis is measured using, for example, FACS analysis of M14, JR8, and PLF2 cells on days 4, 5, 6, 7, and 8 of cell proliferation in the presence and absence of c-myc oligonucleotides.

M14, JR8, and PLF2 cells treated as described above are monitored daily for evidence of apoptosis beginning at the end of treatment and continuing up to 5 days after treatment. The cells are harvested and pooled with their culture fluids. Cell suspensions from NG tumor xenografts, obtainable from mice treated according to schedule c (see Example 8) and with the single bolus (S)ODNs, are also collected. The cell suspension from each sample is divided into two aliquots. One aliquot is used for a morphological analysis (cytospin staining with May-Grunwald/Giemsa solution) and the other aliquot is fixed in ethanol 80% at 4° C. for 60 minutes. The ethanol treated cells are washed twice with PBS, pelleted by centrifugation, and resuspended in a solution containing RNase (50 U/mg; 50 µg/ml) and PI (50 µg/mL). The PI-stained cells are evaluated using a FACScan cytofluorimeter. The logarithmic red PI-fluorescence is measured with a LP 620 filter. Twenty thousand events/sample are accumulated and the list mode data analyzed by Lysis II-C32 Becton Dickinson software.

In a representative FACS experiment with M14 cells on day 7 of growth, about 50% of the cells treated with c-myc antisense (S)ODNs show hypodiploid DNA content indicative of apoptosis. Apoptosis (20% hypodiploid cells) is evident after 48 hours from the end of the treatment (day 6 of growth). "G-quartet"-scrambled (S)ODNs do not cause programmed cell death. The presence of apoptosis is also confirmed by morphological analysis. Similar FACS results are obtainable using the other cell lines and NG tumor cells, as in Example 10.

Thus, the inhibition of cell proliferation is followed by a decrease in cell viability as reflected, at least in part, by the appearance of cells with a hypodiploid DNA content. This is consistent with down-regulation of c-myc by treatment with (S)ODNs complementary and that a decrease c-myc mRNA leads directly, or indirectly, to apoptotic cell death. As described herein, in cells arising from a solid tumor expressing c-myc, the suppression of endogenous c-myc by c-myc oligonucleotides causes the inhibition of cell proliferation and the induction of programmed cell death.

Example 7
c-myc Oligonucleotide and Cisplatin Combination Treatment Inhibits Cell Proliferation More than Treatments with Either c-myc Oligonucleotide or Cisplatin Alone To determine the efficacy of oligonucleotides complementary to c-myc mRNA in combination with cisplastin in the treatment of melanoma, melanoma cells are treated with cisplatin and c-myc (S)ODNs, preferably in a sequential fashion. These experiments show that unexpected result of a syngeristic effect of c-myc oligonucleotide/cisplastin treatments compared to treatment using either drug alone.

Melanoma cells (M14), such as cells used herein, are plated at $8 \times 10^3$ and starting from day 1 after seeding are treated following different schedules: (a) untreated; (b) cisplatin 5 µg/ml for 2 h, on day 1; (c) cisplatin 5 µg/ml for 2 h, on day 5; (d) c-myc oligonucleotide or scrambled (S)ODNs 100 µg/ml on day 1 and 50 µg/ml on days 2–4; (e) c-myc oligonucleotide or scrambled (S)ODNs on days 1–4 followed by cisplatin 5 µg/ml on day 5; and (f) cisplatin 5 µg/ml on day 1 followed by c-myc antisense or scrambled (S)ODNs on days 1–4.

Figure 2:
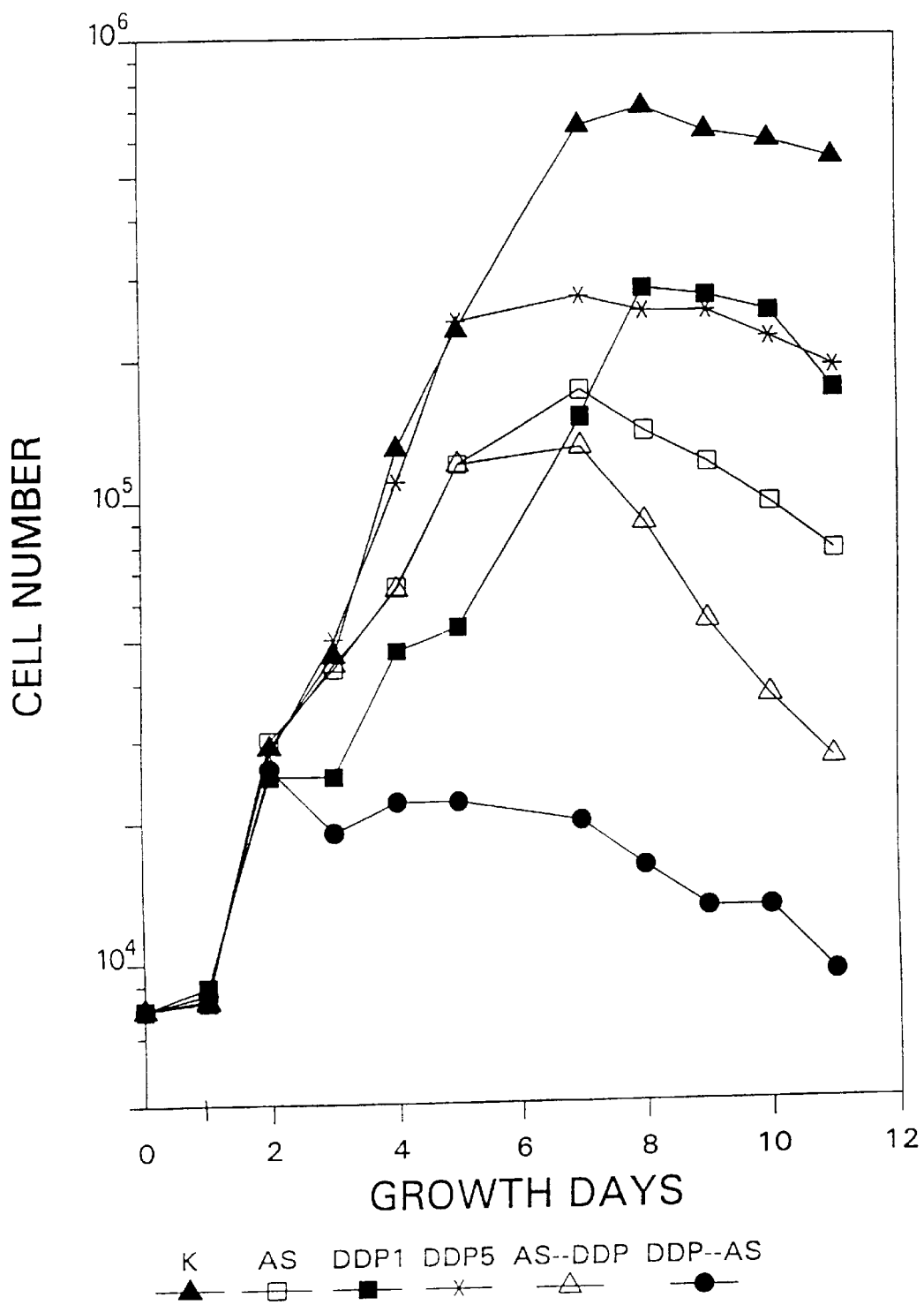
FIG. 2 shows the proliferation of melanoma cells after exposure to c-myc (S)ODNs in combination with cisplatin. Panels: (▲) untreated; (□) c-myc (S)ODNs at 100 µg/ml day 1 and 50 µg/ml days 2–4; (■) cisplatin 5 µg/ml for 2 h, day 1; (*) cisplatin 5 µg/ml for 2h day 5; (Δ) c-myc (S)ODNs days 1–4 followed by cisplatin 5 µg/ml at day 5; (●) cisplatin 5 µg/ml day 1 followed by c-myc (S)ODNs days 1–4.

It is evident from FIG. 2 that treatments with cisplatin and c-myc (S)ODN as in schedule e and f produce a more marked inhibition of cell proliferation than the treatments with cisplatin or c-myc (S)ODNs alone. Treatments with cisplatin followed by c-myc (S)ODNs produced the largest effect. Scrambled (S)ODNs alone have no effects on proliferation of melanoma cells and do not enhance the lethal activity of cisplatin.

Thus, treatment with c-myc (S)ODNs in combination with cisplatin enhances the anti-proliferative effect provided by either drug alone.

Example 8
c-myc Oligonucleotide Treatment Decreases in vivo Tumor Growth in a Dose Dependent Manner To identify the ability of c-myc oligonucleotides to decrease tumor growth in vivo, the human primary melanoma (NG) is transplanted into nude mice and used for in vivo experiments, in which the efficacy of (S)ODNs complementary to c-myc mRNA is evaluated not only in terms of tumor growth inhibition, but also in terms of reduction in the number of metastases and increase in lifespan. This last parameter represents a principal end-point in establishing the antitumor activity of a new drug. Nude mice bearing NG tumors are treated with 0.25 mg, 0.5 mg, or 1 mg (S)ODNs/day for 8 consecutive days, and the dose-response relationship is evaluated.

In vivo administration of (S)ODNs

CD-I male nude mice (nu/nu), 6–8 weeks old and 22–24 g in body weight, are purchased from Charles River Laboratories, Calco, Italy. Mice are housed under pathogen-free conditions and given acidified, autoclaved water and a γ-irradiated commercial diet. All manipulations are done under sterile conditions in a laminar flow hood. All procedures involving animals and their care are in accord with institutional guidelines in compliance with national and international laws and policies (EEC Council Directive 86/609, OJL 358, Dec. 1, 1987, and the National Institute of Health (NIH) Guide for the Care and Use of Laboratory Animals, NIH Publ No. 85-23, 1985). Each experimental group of mice includes at least 6 animals with a maximum of 20 animals for the evaluation of numbers of metastases.

(S)ODNs are administered intravenously starting from day 1 after tumor implant. Histological examination performed at days 2, 4, and 7 after implant reveals indistinguishable tumor organization in control and mice treated with (S)ODNs complementary to c-myc mRNA. To evaluate the antitumor activity of (S)ODNs, different administration schedules are tested: a) 0.25 mg, 0.5 mg or 1 mg of (S)ODNs/mouse/day for 8 consecutive days; b) 0.25 mg or 0.5 mg (S)ODNs/mouse/day for 8 consecutive days followed by a second cycle of treatment after a 7-day interval (i.e. 7 day period of no administration); c) 1 mg (S)ODNs/mouse/day at days 1, 3, 5, and 7 and 0.5 mg (S)ODNs/mouse/day at days 2, 4, 6, and 8, followed by a second cycle of treatment after a 6-day interval. Equivalent doses of sense, scrambled, or "G-quartet"-scrambled (S)ODNs are used as controls. Ten tumor-bearing mice treated with EBSS diluent are included in each experiment.

Assessment of Antitumor Activity and Toxicity

Antitumor activity of (S)ODNs is assessed using the following end-points:

1) percent tumor weight inhibition (TWI %), calculated by dividing the mean tumor weight of the treated group by the mean tumor weight of the control group, minus 1×100;
2) tumor growth delay, evaluated as T-C, where T and C are the median times for treated and control tumors, respectively, to reach the same size (500 mg);
3) metastases reduction;
4) percent increase in life span (ILS %).

Tumor weight is calculated using caliper measurements according to the method of Geran et al. (Geran et al., *Cancer Chemother. Rep.* 3:1–88 (1972)), using the formula: tumor weight (mg)=length (mm)×width (mm)$^2$/2. To estimate the metastatic potential of NG melanoma, tumor-bearing mice are sacrificed 28 days after tumor implant. The lungs of the mice are removed and fixed in Bouin's solution in order to evaluate tumor nodules from lung tissue. The numbers of metastases are determined with the aid of a dissecting microscope.

Toxicity is assessed on the basis of apparent drug-related deaths and net body weight loss. Death in a treated mouse is presumed to be treatment-related if the mouse dies within 7 days after the last treatment. Net body weight loss is calculated as a percentage of mean net body weight of untreated mice. Necropsy is performed on dead mice, and livers, spleens, and lungs were examined histologically.

Results

As shown in FIG. 3A (see also Table 3), a marked dose-dependent decrease in tumor growth is observed after treatment with (S)ODNs complementary to c-myc mRNA. Treatment with 0.25 mg per day (schedule a, Table 3) is less effective than treatment with 0.5 or 1 mg per day (schedules b and c, Table 3). The maximum effect on tumor growth is evident at day 16 after tumor implantation (1 week after the end of treatment). At this time, the tumor growth delay is 3 days in mice treated with the lowest dose, and 8 days and 13 days in mice treated with 0.5 mg/day and 1 mg/day, respectively. No toxicity is observed in mice receiving either 0.5 mg or 0.25 mg/day of (S)ODNs complementary to c-myc mRNA for 8 days. In contrast, marked toxicity (50% death) is observed with 1 mg/day of antisense (S)ODNs given for 8 days, making this schedule unsuitable even though there is a significant antitumor effect. A toxic death rate of about 20% is also observed in mice treated with 1 mg per day of scrambled or sense (S)ODNs, but tumor growth is unaffected. Necropsy on the mice that do not survive the 1 mg/day treatment should reveal splenomegaly and adenopathy of axillary and inguinal lymph nodes, but without a loss in body weight.

Example 9

Optimization of Therapeutic Index of c-myc Oligonucleotides in vivo

To optimize the therapeutic index of (S)ODNs complementary to c-myc mRNA (c-myc (S)ODNs), repeated cycles of treatment using 0.25 mg or 0.5 mg (S)ODNs/mouse/day for 8 consecutive days for two cycles at 1-week intervals are evaluated. The repeated administration of the (S)ODNs complementary to c-myc mRNA improves the antitumor efficacy, as shown in FIG. 3B and Table 3. In fact, a tumor weight inhibition of 56% (p=0.0095 vs control and scrambled ODNs-treated mice) and 68% (p=0.0004 vs control and scrambled ODNs-treated mice) is observed after treatment with a total dose of 4 mg/mouse (schedule g) and 8 mg/mouse (schedule h), respectively of c-myc oligonucleotide. Note that, while the injection of 1 mg/mouse day for 8 days (total dose 8 mg/mouse) produces a marked toxicity, administration of the same total dose but given during repeated cycles enhances the antitumor activity of c-myc (S)ODNs and decreases toxicity. On the basis of these results, a total dose of 12 mg of c-myc (S)ODNs is also used. Control mice are treated with 1 mg of c-myc (S)ODNs, scrambled, or "G-quartet"-scrambled (S)ODNs on days 1, 3, 5, and 7 and 0.5 mg on days 2, 4, 6, and 8 (schedules i, l, and m, respectively) after tumor implantation. Six days after the first cycle, the treatment is repeated with the same fractionated doses. This schedule is the most effective (see FIG. 3C and Table 3), as indicated by the marked increase in tumor weight inhibition.

Table 3 summarizes the main end points evaluated after (S)ODN treatment. The therapeutic efficacy of c-myc (S)ODNs can be enhanced by dose and schedule. A significant reduction in the number of lung metastases (p=0.02, comparison of schedules h, k, and i[1]) is accompanied by a significant increase in animal survival. In particular, alternate doses of 1 mg and 0.5 mg for 8 consecutive days, repeated after a 6-day interval, reduces tumor weight by approximately 80% (p=0.0012 vs control and p=0.0013 vs scrambled ODNs-treated tumors) and delays tumor regrowth by 16 days (p=0.001 vs control and p=0.0016 vs scrambled ODNs-treated tumors). Treatment with scrambled or "G-quartet" scrambled (S)ODNs has no effect on tumor growth.

The therapeutic index of c-myc (S)ODNs can be related to the schedule of administration. In fact, a total dose of 8 mg/mouse given in a single cycle of treatment for 8 consecutive days (1 mg/mouse/day) causes a high toxicity with a 50% death rate. By contrast, the same dose, administered in two repeated cycles is not toxic. Moreover, 1 mg/day of sense and scrambled (S)ODNs given for 8 consecutive days causes toxic effects, in the absence of antitumor activity. Nonspecific toxicity likely reflects some physico-chemical property of phosphorothioate compounds. Histopathologic examination of the mice should reveal splenomegaly, consistent with observations in animals treated with c-myc (S)ODNs and with (S)ODNs complementary to the rev gene of HIV-1 (Hijiya et al., *Proc Natl Acad Sci USA* 91:4499–4503 (1994); Branda et al., *Biochem Pharmacol* 45:2037–2043 (1993)). The recent demonstration that some oligonucleotide sequences stimulate the proliferation of B-lymphocytes in vitro (Krieg et al., *Nature* 374:546–549 (1995)) and the postulated immunoregulatory function of certain (S)ODNs (Mojcik et al., *Clin Imnunol Immunopathol* 67:130–136 (1993)) could explain the splenomegaly observable in several animal models.

The use of fractionated doses (i.e. spreading the dose over time) increases the total amount of (S)ODNs administered, reduces toxicity, and increases antitumor activity. As reported in Table 3, a total dose of 12 mg/mouse administered in alternate doses of 1 and 0.5 mg/day for 8 consecutive days and repeated after a 6-day interval, induces an 80% inhibition of tumor growth and a 46% increase in life span in the absence of toxicity. Likewise, it is known in the art that control severe combined immunodeficiency (SCID) mice injected with routine (S)ODNs complementary to c-myc mRNA at similar doses suffer no major toxicity-associated morphological changes in many organs examined and no decrement in the proliferative capacity of bone marrow cells as indicated by clonogenic assays. Thus, (S)ODNs are devoid of long term storage toxicity.

Example 10 c-myc Oligonculeotide Treatment Decreases c-myc Expression and Increases Apoptosis in vivo To establish whether the antitumor effect observed in vivo is due to interference with c-myc expression by c-myc (S)ODNs, c-myc expression is evaluated in NG melanoma by FACS analysis following in vivo administration of c-myc (S)ODNs. Tumor-bearing mice (3 animals per group) are treated with c-myc (S)ODNs or scrambled (S)ODNs according to schedule c (see Table 3). An additional group of 3 untreated tumor-bearing mice are injected with a single bolus of 2.5 mg antisense or scrambled (S)ODNs/mouse at day 23 after tumor implantation. Twenty-four hours after the end of each treatment, the mice are sacrificed and the tumors are excised. Tumor samples from animals of each group are pooled and minced carefully with a sharp blade. Samples containing $2 \times 10^6$ cells are fixed in acetone-methanol (1:4, v/v) in 50% PBS at 4° C., washed in IFA buffer (10 mM Hepes, 150 mM NaCl, 4% fetal calf serum, [pH 7.4]) and incubated for 5 minutes in IFA buffer containing 0.2% Tween 20 (Sigma, St. Louis, Mo., USA). Indirect immunofluorescence is performed using the same anti-Myc primary antibody used in the western blot analysis and a fluorescinated rabbit anti-mouse $F(ab')_2$ (DAKO, Glostrup, Denmark). Samples are resuspended in PBS and analyzed in a FACScan cytofluorimeter. Logarithmic green fluorescence of the FITC labeled anti-Myc antibody is monitored using a BP 530/15 filter. Ten thousand events are stored for each sample, and the list mode data analyzed using Lysis II-C32 Becton Dickinson software. The percentage of c-myc-positive cells is evaluated after subtracting the background (2% to 5%) in each histogram.

Figure 4G:
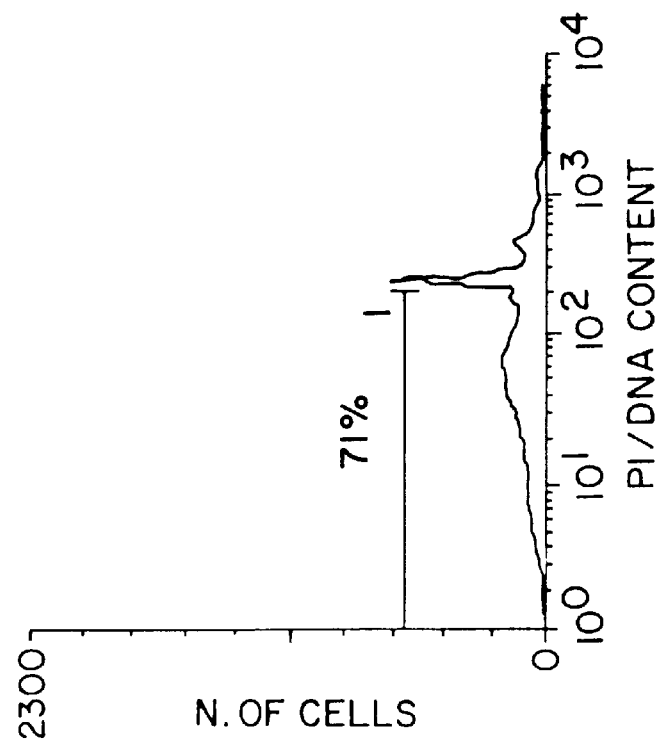

FACS analysis shows that 85% of NG melanoma cells are c-myc-positive (FIG. 4A). In addition, analysis of DNA content histograms of tumor cells from control mice reveals an accumulation in the hypodiploid region, representing about 30% of the cell population (FIG. 4E, inset), indicating apoptotic cell death. This cell death is expected since the FACS analysis is performed when tumors were at a late stage of growth (day 24 of growth). Similar levels of Myc expression (87% positivity) and apoptosis (31%) are found in tumor cells from scrambled-treated mice (FIGS. 4B and 4F). In contrast, treatment with c-myc (S)ODNs produces a marked decrease in c-myc expression, with only 12.9% of Myc-positive cells (FIG. 4C). Furthermore, the percentage of apoptotic tumor cells is increased (to about 70%) (FIG. 4G). To determine whether the decrease in c-myc expression is due to c-myc down-regulation induced by the c-myc (S)ODNs, and not merely related to the apoptotic status of the cell population, c-myc protein expression is analyzed in an early phase of treatment. At 23 days after NG tumor implantation, mice are injected with a single bolus of 2.5 mg scrambled or c-myc (S)ODNs, and 24 hours later, the tumors are excised and c-myc expression is evaluated by FACS analysis. As shown in FIG. 4D, treatment with c-myc (S)ODNs results in a 65% inhibition of protein expression, whereas no evidence of an increase in apoptosis is observed (FIG. 4H, inset). Treatment with a single bolus of scrambled (S)ODNs has no effect on Myc expression and apoptosis. The fact that the decrease in c-myc expression is also observed as early as 24 hours after treatment with a single bolus, when the antitumor effect was not yet evident, confirms that the decreased c-myc expression is specifically related to treatment with c-myc (S)ODNs.

The morphology of tumor cells from untreated or (S)ODN-treated mice is studied on cytospin preparations after May-Grunwald/Giemsa staining. In tumor cells obtained from control or scrambled (S)ODN-treated mice, the morphological pattern indicative of apoptosis is consistent with the physiological percentage of programmed cell death observed by FACS analysis. A greater percentage of tumor cells derived from antisense-treated mice exhibit characteristics of apoptosis, such as loss of cell volume (cell shrinkage), nuclear condensation, and a prominence of apoptotic bodies. The morphological characteristics of tumor cells from mice injected with the single bolus c-myc (S)ODNs and analyzed at early times are nearly identical to those of control cells.

Thus, programmed cell death in vivo is more pronounced in tumors from mice treated with (S)ODNs complementary to c-myc mRNA as compared with tumors from untreated or scrambled-treated mice. The dose-response relationship and the absence of an antitumor effect of the sense and scrambled (S)ODN controls also demonstrates that the (S)ODNs complementary to c-myc mRNA (c-myc (S)ODNs) are responsible for the antitumor activity. Demonstration of c-myc (S)ODN sequence specificity for the down-regulation of c-myc levels in the NG tumor after in vivo treatment also further confirms that c-myc expression is specifically reduced.

Example 11 c-myc Oligonucleotides and Cisplatin in Combination Inhibit Tumor Growth in Vivo More Than Either c-myc (S)ODN or Cisplatin Alone To demonstrate the in vivo effect of c-myc oligoncueoitde/cisplatin treatment on tumor growth, c-myc oligonucleotide/cisplatin combination treatment was compared to treatments eith c-myc oligonucleoitde or cisplatin alone. Combination therapy produced an enhanced therapeutic efficacy compared to the administration of either drug alone.

Mice are treated with cisplatin followed by (S)ODNs complementary to c-myc mRNA (c-myc (S)ODNs). A melanoma tumor is implanted i.m. in nude mice as described herein. Treatment starts at day 4 after tumor implant when tumor is evident in all the mice injected. Treatments are described according to the following schedules: Control (untreated mice); Schedule 1 (n=10): cisplatin i.p. 3.3 mg/Kg days 4–6; Schedule 2 (n=10): c-myc (S)ODN i.v. 1 mg/mouse at days 7, 9, 11, 13 and 0.5 mg/mouse at days 8, 10, 12, 14; and Schedule 3 (n=10): cisplatin days 4–6 followed by antisense days 7–14. After the second cycle of treatment, mice (schedule n.3) are randomized in two groups of 4 mice each, although schedule 3 originally started with 10 mice. In schedule 3 one mouse died 3 days after first cycle of treatment concluded, and one mouse was sacrificed just before the start of third cycle to evaluate toxicity. After 7 days the end of the second cycle, four mice from schedule 3 received a third cycle of cisplatin followed by c-myc (S)ODN (FIG. 5 and in Table 4).

The treatment of mice with cisplatin followed by c-myc (S)ODNs produces a marked increase in tumor weight inhibition and in tumor growth delay as compared to mice treated with cisplatin or c-myc (S)ODN alone.

TABLE 3

Therapeutic efficacy of c-myc oligonucleotides in NG tumor bearing mice.

| | Schedule[1] | Total dose mg/mouse | TWI\|[1] % | TWI\|2 % | T-C[2] days | Toxic deaths | Median no. of metastases[3] | ILS[4] % |
|---|---|---|---|---|---|---|---|---|
| a) | AS 0.25 mg/d × 8 days | 2 | 52(38–88)}} | — | 8(1.5–4.5) | 0/8 | N.E.[5] | 5(4–6) |
| b) | AS 0.5 mg/d × 8 days | 4 | 59(42–76)}} | — | 8(8–10)} | 1/8 | N.E. | 18(9–17) |
| c) | AS 1 mg/d × 8 days | 8 | 76[5] | — | 12[5] | 4/8 | 4(3–8)[5] | N.E. |
| d) | SS 0.25 mg/d × 8 days | 2 | 2(1.5–2.5) | — | 0 | 0/8 | N.E. | 0 |
| e) | SS 0.5 md/d × 8 days | 4 | 10(7–13) | — | 1(0.8–1.2) | 0/8 | N.E. | 0 |
| f) | SS 1 mg/d × 8 days | 8 | 3(2.6–3.4) | — | 3(2.4–3.6) | 1/8 | 26(18–65) | N.E. |
| g) | AS 0.25 mg/d × 8 days | 4 | 51(36–66)}} | 58(37–75)}} | 6.5(4–9)} | 1/9 | N.E. | 21(9–33) |
| h) | AS 0.5 mg/d × 8 days | 8 | 61(48–74)}} | 88(53–83)}} | 10(8–12)}} | 2/20 | 15(7.18)} | 50(39–81)} |
| i) | AS 1 mg/d × 8 days at days 1, 3, 5, 7 and 0.5 mg/d at days 2, 4, 6, (repeated) | 12 | 71(47–100)}} | 80(52–100)}} | 16(11–21)}} | 0/8 | N.E. | 46(32–58)} |
| i[1]) | AS 1 mg/d at days 1, 3, 5, 7 and 0.5 mg/d at days 2, 4, 6, 8 | 12 | 75(49–100)}} | 82(51–100)}} | 17(12–22)}} | 0/6 | 13(4–21)} | N.E. |
| j) | SS 0.25 mg/d × 8 days | 4 | 3(1.5–4.5) | 3(1.6–4.4) | 0 | 0/8 | N.E. | 0 |
| k) | SS 0.5 mg/d × 8 days | 8 | 3(2.5–3.5) | 2(1.8–2.2) | 0 | 0/17 | 25(12–55) | 10(7–13) |
| l) | SS 1 mg/d 1, 3, 5, 7 and 0.5 mg/d at days 2, 4, 6, 8 | 12 | 15(10–20) | 16(10–22) | 2(1–3) | 0/8 | N.E. | 11(6–16) |
| l[1]) | SS 1 mg/d at days 1, 3, 5, 7 and 0.5 mg/d at days 2, 4, 6, 8 | 12 | 5(3–7) | 7(4.5–9.5) | 1(0.7–1.9) | 0/8 | 26(14–62) | N.E. |
| m) | G-quartet 1 mg/d at days 1, 3, 5, 7 and 0.5 mg/d at days 2, 4, 6, 8 | 12 | 6(3–9) | 6(3.5–8.5) | 2(1.6–2.4) | 0/8 | N.E. | 7(5–9) |

TABLE 3

LEGEND

Mice were treated from day 1 after tumor implant with antisense ("AS"), scrambled (SC) or "G-quartet" (S)ODNs following different schedules.

a, d: 0.25 mg/mouse/day for 8 days,
  b, e: 0.5 mg/mouselday for 8 days,
  c, f: 1 mg/mouse/day for 8 days.
  g, j: 0.25 mg/mouse/day for 8 days. A second cycle was repeated after a 7-day interval time.
  h, k: 0.5 mg/mouse/day for 8 days. A second cycle was repeated after a 7-day interval time.
  i.i[1], 1,1[1], m: 1 mg/mouse at days 1, 3, 5, 7 and 0.5 mg/mouse at days 2, 4, 6, 8. A second cycle was repeated after a 6-day interval. Untreated mice received diluent only.

§   Tumor weight inhibition (mean tumor weight of the treated group divided by the mean tumor weight of the control group, minus 1 × 100). Calculated after the 1st (1) and the 2nd (2) cycle at nadir of the effect. In parentheses, 95% confidence intervals.

2   Tumor growth delay (median times in days for treated and control tumors to reach the size of 500 mg.). In parentheses, 95% confidence intervals.

3   The median no. of metastases in untreated group for schedules c and f was 28 (10–70), for schedules h and k was 27 (13–69) and for schedules i[1] and 1[1] was 24 (10–57). Range, in parentheses.

N.E., not evaluated.

4   Increase in life span. In parentheses, 95% confidence intervals.

5   Because of the small number of mals survived in this schedule, statistical analysis was not performed and confidence intervals have not been calculated.

◇ ◇   $p < 0.01$, ◇ $< 0.05$ (two-sided) versus scrambled and untreated mice.

TABLE 4

THERAPEUTIC EFFICACY OF c-myc ANTISENSE AND CISPLATIN (DDP) IN COMBINATION ON NG TUMOR BEARING MICE

| SCHEDULE | TWI[1] % | TWI[2] % | TWI[3] % | T-C (DAYS) | TOXIC DEATHS |
|---|---|---|---|---|---|
| Untreated | 100 | 100 | 100 | — | — |
| DDP (schedule 1) | 60 | 69 | 64 | 14 | 0/10 |
| AS (schedule 2) | 53 | 57 | 70 | 11 | 0/10 |
| DDP→AS (2 cycles, schedule 3) | 85 | 92 | 87 | 31 | 1/10 |
| DDP→AS (3 cycles, schedule 3) | 85 | 92 | 97 | 45 | 0/4 |

Tumor weight inhibition (TWI) were analyzed by the Mann-Whitney U-test for statistical significance. TWI1 refers to TWI after one cycle. TWI2 refers to TWI after two cells. Because of the small number of animals in the groups DDP→AS the statistical analysis was not performed after the third cycle of treatment. Results are as follows:

| | | | | |
|---|---|---|---|---|
| TWI[1]: | DDP | vs | Untreated | p = 0.00018 |
| | AS | vs | Untreated | p = 0.00025 |
| | DDP→AS | vs | Untreated | p = 0.0003 |
| | DDP→AS | vs | DDP | p = 0.00028 |
| | DDP→AS | vs | AS | p = 0.00025 |
| | DDP | vs | AS | p = 0.05 |
| TWI[2]: | DDP | vs | Untreated | p = 0.00001 |
| | AS | vs | Untreated | p = 0.0002 |
| | DDP→AS | vs | Untreated | p = 0.0003 |
| | DDP→AS | vs | DDP | p = 0.0001 |
| | DDP→AS | vs | AS | p = 0.0001 |
| | DDP | vs | AS | p > 0.05 |

PUBLICATIONS

1. Agrawal et al., Proc Natl Acad Sci USA 88:7595–7599 (1991)
2. Arad et al., *Biochem. Biophy. Acta.,* 859:88–94 (1986)
3. Battey et al, *Cell,* 34:779–787 (1983)
4. Beal and Dervan, *Nucleic Acids Research,* 20:2773–2776 (1992)

5. Beal and Dervan, *J. Am. Chem. Soc.,* 114:4976–4982 (1992)
6. Beaucage and Iyer, *Tetrahedron,* 48:2223–2311 (1992)
7. Bergot, U.S. Pat. No. 5,183,885
8. Blume et al, *Nucleic Acids Research,* 20:1777–1784 (1992)
9. Branda et al., *Biochem Pharmacol* 45:2037–2043 (1993)
10. Caruthers and Nielsen, International application PCT/US89/02293
11. Caruthers et al, U.S. Pat. No. 4,415,732
12. Caruthers et al, U.S. Pat. No. 4,458,066
13. Caruthers et al, U.S. Pat. No. 4,973,679
14. Chenevix-Trench et al., *Oncogene* 5:1187–1193 (1990)
15. Cheng et al, *J. Am. Chem. Soc.,* 114:4465–4474 (1992)
16. Chomczysky et al., *Anal Biochem* 162:156–159 (1987)
17. Citro et al., *Proc. Natl. Acad. Sci. USA,* 89:70331–7035 (1992)
18. Crooke, *Ann. Rev. Pharmacol. Toxicol.* 32:329–376 (1992)
19. Dagle et al., *Antisense Res Dev* 1:11–20 (1991)
20. Distefano et al, *Proc. Natl. Acad. Sci.,* 90:1179–1183 (1993)
21. Dugaiczyk et al., *Biochemistry* 22:1605–1613 (1983)
22. Eder et al., *Antisense Res Dev i:*141–151 (1991)
23. Epstein et al, *NTIS publication PB*93-100576
24. Evan et al., *Mol Cell Biol* 5:3610–3616 (1985)
25. Feinberg et al., *Anal. Biochem.* 132:6 (1983)
26. Froegler et al, International application PCT/US90/03138
27. Froehler et al, *Tetrahedron Lett.,* 33:5307–5310 (1992)
28. Gazin et al, *E.M.B.O. Journal* 32:383–387 (1984)
29. Gennaro, Alfonso, ed., *Remington's Pharmaceutical Sciences,* 18th Edition, 1990, Mack Publishing Co., Easton, Pa.
30. Geran et al., *Cancer Chemother. Rep.* 3:1–88 (1972)
31. Giovannangeli et al, *Proc. Natl. Acad. Sci. USA,* 89:8631–8635 (1992)
32. Goodchild et al, U.S. Pat. No. 4,806,463
33. Greco et al, *Tumori* 65:169–180 (1979)
34. Greco et al., *Anticancer Res* 7:839–844 (1987)
35. Hijiya et al., *Proc Natl Acad Sci USA* 91:4499–4503 (1994)
36. Hirschbein, U.S. Pat. No. 5,166,387
37. Jager et al, *Biochemistry,* 27:7237–7246 (1988)
38. Kimura et al., *Cancer Res.* 55:1379–1384 (1995)
39. Koster et al, U.S. Pat. No. 4,725,677
40. Krieg et al., *Nature* 374:546–549 (1995)
41. Laemmli UK *Nature* 227:681–685 (1970)
42. Lemaiture et al., *Proc. Natl. Acad. Sci. USA,* 84:648–652 (1987)
43. Lesnikowski, *Bioorgc Chemistry,* 21:127–155 (1993)
44. Letsinger et al, *Proc. Natl. Acad. Sci. USA,* 86:6553–6556 (1989)
45. Liposome Technology, Vol. II, *Incorporation of Drugs, Proteins and Genetic Material* (CRC Press)
46. Lombardi et al., *Cell* 49:161–170 (1987)
47. Marcu et al, *Ann. Rev. Biochem.,* 61:809–860 (1992)
48. Marshall et al, *Science,* 259:1564–1570 (1993)
49. Matteucci et al, International application PCT/US91/06855
50. McShan et al, *J. Biol. Chem.,* 267:5712–5721 (1992)
51. Mergny et al, *Biochemistry,* 30:9791–9798 (1991)
52. Miller et al, U.S. Pat. No. 4,507,433
53. Miller et al, U.S. Pat. No. 4,757,055
54. Milligan et al, *J. Med. Chem.,* 36:1923–1937 (1993)
55. Mojcik et al., *Clin Immunol Immunopathol* 67:130–136 (1993)
56. Molko et al, U.S. Pat. No. 4,980,460
57. Moser and Dervan, *Science,* 238:645–650 (1987)
58. Mottolese et al., *Melanoma Res.* 4:53–58 (1994)
59. Nielsen et al, *Anti-cancer Drug Design,* 8:53–63 (1993), International application PCT/EP92/01220
60. Peyman and Ulmann, *Chemical Reviews,* 90:1543–584 (1990)
61. *Remington's Pharmaceutical Science,* latest edition (Mack Publishing Company, Easton, Pa.)
62. Roberts et al, *Proc. Natl. Acad. Sci. USA,* 88:9397–9401 (1991)
63. Roberts et al, *Science,* 258:1463–1466 (1992)
64. Rosenberg et al, International application PCT/US92/05305
65. Sambrook J, Fritsch E F, Maetis T: *Molecular cloning: a laboratory manual. Cold Spring*
66. Shea et al, *Nucleic Acids Research,* 18:3777–3783 (1990)
67. Spielvogel et al, U.S. Pat. No. 5,130,302
68. Stec et al, U.S. Pat. No. 5,151,510
69. Stec et al, European patent application 92301950
70. Stein et al., *Nucleic Acid Res* 16:3209–3221 (1988)
71. Szostak et al, *Meth. Enzymol.* 68:419–429 (1979)
72. Ts'o et al, U.S. Pat. No. 4,469,863
73. Ulmann et al, *Chemical Reviews,* 90:543–584 (1990)
74. Wagner et al., *Proc. Natl. Acad. Sci. USA,* 87:3410–3414 (1990)
75. Watt et al, *Nature,* 303:725–728 (1983)
76. Wickstrom et al., *J Biochem Biophys Methods* 13:97–102 (1987)
77. Yaswen et al., *Antisense Res Dev* 3:67–77 (1993)
78. Yoon et al, *Proc. Natl. Acad. Sci. USA,* 89:3840–3844 (1992)
79. Zamecnik and Stephenson, *Proc. Natl. Acad. Sci,* 75:280–284 (1974)
80. Zon and Geiser, *Anti-Cancer Drug Design,* 6:539–568 (1991)
81. Zupi et al., *Proc Am Assoc Cancer Res* 26:22 (1985)

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A method of inhibiting proliferation of human melanoma cancer cells comprising: administering to a patient having a melanoma a c-myc oligonucleotide in an amount sufficient to inhibit said proliferation, wherein said c-myc oligonucleotide is complementary to a nucleotide sequence of human c-myc mRNA; and
   wherein said c-myc oligonucleotide is at least 10 bases in length and inhibits proliferation of cultured human melanoma cells by at least 10% at a concentration of 10 $\mu$M compared to proliferation of cultured said human melanoma cells in the absence of said c-myc oligonucleotide and said human melanoma cells are cultured in the presence of serum at 37° C.

2. The method of claim 1, wherein said c-myc oligonucleotide kills said melanoma cancer cells.

3. The method of claim 2, wherein said c-myc oligonucleotide induces apoptosis of said melanoma cancer cells.

4. The method of claim 3, wherein said melanoma cancer cells form a tumor.

5. The method of claim 4, wherein said c-myc oligonucleotide is at least 12 bases in length and has nuclease resistant internucleoside linkages.

6. The method of claim 5, wherein said nuclease resistant internucleoside linkages are selected from the group consisting of phosphorothioate, phosphorodithioate, phosphoroanilothioate, phosphoranilidate, phosphoramidate, and N3'→P5' phosphoramidate linkages.

7. The method of claim 6, wherein said c-myc oligonucleotide is complementary to an ATG translation initiation region of said mRNA.

8. The method of claim 6, wherein said c-myc oligonucleotide has phosphorothioate or N3'→P5' phosphoramidate linkages.

9. The method of claim 8, wherein said c-myc oligonucleotide is a member selected from the group consisting of SEQ ID NO: 1, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 14, SEQ ID NO: 15, SEQ ID NO: 16, SEQ ID NO: 17.

10. The method of claim 9, further comprising contacting said human melanoma cancer cells with a cisplatin compound.

11. The method of claim 10, wherein said cisplatin compound is administered first and said c-myc oligonucleotide is formulated in a liposome.

12. The method of claim 10, wherein said administering comprises topically applying said c-myc oligonucleotide and said cisplatin compound.

13. The method of claim 10, wherein said administering comprises topically applying or non-systemically injecting said c-myc oligonucleotide and said cisplatin compound after surgical removal of said human melanoma tumor.

14. The method of claim 10, wherein said administering comprises systemically injecting said human melanoma tumor with said c-myc oligonucleotide and said cisplatin compound.

15. The method of claim 1, wherein said c-myc oligonucleotide is formulated in a liposome.

16. The method of claim 1, wherein said c-myc oligonucleotide comprises SEQ ID NO: 1 formulated in a liposome.

17. The method of claim 1, wherein said c-myc oligonucleotide is entrapped in a liposome.

18. The method of claim 1, wherein said c-myc oligonucleotide is formulated with a pharmaceutically acceptable carrier.

19. The method of claim 1, wherein said c-myc oligonucleotide is conjugated to a ligand binding molecule that recognizes a cell-surface molecule.

20. The method of claim 1, wherein said c-myc oligonucleotide is contained in an expression plasmid.

21. The method of claim 1, wherein said mode of administering is a member selected from the group consisting of: intranasally, intravenously, transdermally, topically, by implantation, parentally, intraperitoneally, subcutaneously, orally, systemically, by absorption, and combinations thereof.

22. The method of claim 21, wherein said c-myc oligonucleotide is formulated in a member selected from the group consisting of: a tablet, a capsule, a lozenge, a troche, a powder, a syrup, an elixir, an aqueous solution and a suspension.

23. The method of claim 21, wherein said c-myc oligonucleotide is in a topical formulation which is a member selected from the group consisting of: a cream, an ointment, a gel, an emulsion and a lotion.

24. A method of inhibiting human melanoma tumor growth comprising:
   administering an effective amount of a c-myc oligonucleotide to a patient in need thereof and said c-myc oligonucleotide is complementary to a nucleotide sequence of human c-myc mRNA,
   wherein said c-myc oligonucleotide inhibits proliferation of cultured human melanoma cells by at least 10% at a concentration of 10 $\mu$M compared to proliferation of cultured human melanoma cells in the absence of said c-myc oligonucleotide and said human melanoma cells are cultured in the presence of serum at 37° C.

25. The method of claim 24, said c-myc oligonucleoitde inhibits metastasis of melanoma cancer cells.

26. The method of claim 24, said c-myc oligonucleotide promotes regression of said human melanoma tumor.

27. The method of claim 24, said c-myc oligonucleotide prevents said human melanoma tumor from increasing in tumor in mass.

28. The method of claim 25, wherein said c-myc oligonucleotide is at least 12 bases in length and has nuclease resistant internucleoside linkages.

29. The method of claim 28, wherein said nuclease resistant internucleoside linkages are selected from the group consisting of phosphorothioate, phosphorodithioate, phosphoroanilothioate, phosphoranilidate, phosphoramidate, and N3'→P5' phosphoramidate linkages.

30. The method of claim 29, wherein said c-myc oligonucleotide is complementary to an ATG translation initiation region of said mRNA.

31. The method of claim 30, wherein said c-myc oligonucleotide has phosphorothioate or N3'→P5' phosphoramidate linkages.

32. The method of claim 31, wherein said c-myc oligonucleotide is a member selected from the group consisting of SEQ ID NO: 1, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 14, SEQ ID NO: 15, SEQ ID NO: 16, SEQ ID NO: 17.

33. The method of claim 32, further comprises administering to said patient an effective amount of a cisplatin compound.

34. The method of claim 33, wherein said cisplatin is administered first followed by a c-myc oligonucleotide formulated in a liposome.

35. The method of claim 33, wherein said administering comprises topically applying said c-myc oligonucleotide and said cisplatin compound.

36. The method of claim 35, wherein said administering comprises systemically injecting cisplatin compound and then systemically injecting said c-myc oligonucleotide, wherein said c-myc oligonucleotide decreases the chemoresistance of said human melanoma tumor to cisplatin.

37. The method of claim 35, wherein said administering comprises systemically injecting said c-myc oligonucleotide and then systemically injecting said cisplatin compound.

38. The method of claim 33, wherein said administering comprises topically applying or non-systemically injecting said c-myc oligonucleotide and said cisplatin compound after surgical removal of said human melanoma tumor.

39. The method of claim 33, wherein said administering comprises systemically injecting into said human melanoma tumor said c-myc oligonucleotide and said cisplatin compound.

40. The method of claim 24, wherein said c-myc oligonucleotide is formulated in a liposome.

41. The method of claim 24, wherein said c-myc oligonucleotide is entrapped in a liposome.

42. The method of claim 24, wherein said c-myc oligonucleotide is formulated with a pharmaceutically acceptable carrier.

43. The method of claim 24, wherein said c-myc oligonucleotide is conjugated to a ligand binding molecule that recognizes a cell-surface molecule.

44. The method of claim 24, wherein said c-myc oligonucleotide is contained in an expression plasmid.

45. The method of claim 24, wherein said c-myc oligonucleotide comprises SEQ ID NO: 1 formulated in a liposome.

46. The method of claim 24, wherein said mode of administering is a member selected from the group consisting of: intranasally, intravenously, transdermally, topically, by implantation, parentally, intraperitoneally, subcutaneously, orally, systemically, by absorption, and combinations thereof.

47. The method of claim 46, wherein said c-myc oligonucleotide is formulated in a member selected from the group consisting of: a tablet, a capsule, a lozenge, a troche, a powder, a syrup, an elixir, an aqueous solution and a suspension.

48. The method of claim 46, wherein said c-myc oligonucleotide is in a topical formulation which is a member selected from the group consisting of: a cream, an ointment, a gel, an emulsion and a lotion.

* * * * *